(12) United States Patent
Yagyu et al.

(10) Patent No.: US 11,279,664 B2
(45) Date of Patent: Mar. 22, 2022

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Daisuke Yagyu, Tokyo (JP); Yuta Yamaguchi, Tokyo (JP); Naoya Fukumoto, Tokyo (JP); Tsuyoshi Kato, Tokyo (JP); Shoko Uetake, Tokyo (JP); Hiroyuki Tomita, Tokyo (JP); Ryuuta Miyasaka, Tokyo (JP); Naoko Ito, Tokyo (JP); Ichiro Ota, Tokyo (JP); Katsumi Murofushi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 779 days.

(21) Appl. No.: 16/082,349

(22) PCT Filed: Jan. 30, 2017

(86) PCT No.: PCT/JP2017/003165
§ 371 (c)(1),
(2) Date: Sep. 5, 2018

(87) PCT Pub. No.: WO2017/154403
PCT Pub. Date: Sep. 14, 2017

(65) Prior Publication Data
US 2019/0084911 A1    Mar. 21, 2019

(30) Foreign Application Priority Data
Mar. 10, 2016 (JP) ............................. JP2016-047359

(51) Int. Cl.
*C07C 43/23* (2006.01)
*C10M 105/54* (2006.01)
(Continued)

(52) U.S. Cl.
CPC .......... *C07C 43/23* (2013.01); *C07C 43/1786* (2013.01); *C07D 277/24* (2013.01);
(Continued)

(58) Field of Classification Search
CPC ................ C07C 43/23; C07C 43/1786; C07D 227/24; C07D 303/26; C07D 333/16;
(Continued)

(56) References Cited

U.S. PATENT DOCUMENTS 10,803,898 B2 * 10/2020 Fukumoto ............ C08G 65/007
11,011,200 B2 *  5/2021 Uetake .................. C07C 43/137
(Continued)

FOREIGN PATENT DOCUMENTS

CN      101121908 A     2/2008
EP      1 479 753 A2    11/2004
(Continued)

OTHER PUBLICATIONS

Office Action dated Dec. 2, 2020 from the China National Intellectual Property Administration in CN Application No. 201780012469.9, Partial Translation.
(Continued)

*Primary Examiner* — Holly Rickman
(74) *Attorney, Agent, or Firm* — Sughrue Mion, PLLC

(57) ABSTRACT

The present invention relates to a fluorine-containing ether compound represented by Formula (1), $$R^1—R^2—CH_2—R^3—CH_2—R^4 \quad (1).$$

(In Formula (1), $R^1$ is an end group including an organic group having at least one double bond or triple bond, $R^2$ is a divalent linking group bonded to $R^1$ by etheric oxygen, $R^3$ is a perfluoropolyether chain, $R^4$ is an end group having two or three polar groups with each polar group being bonded to different carbon atoms, and the carbon atoms, to which the (Continued)

polar groups are bonded, being bonded to each other via a linking group including carbon atoms to which the polar groups are not bonded.)

10 Claims, 1 Drawing Sheet

(51) Int. Cl.
*G11B 5/725* (2006.01)
*C10M 107/38* (2006.01)
*C07C 43/178* (2006.01)
*C07D 277/24* (2006.01)
*C07D 303/26* (2006.01)
*C07D 333/16* (2006.01)
*C07D 409/12* (2006.01)
*G11B 5/733* (2006.01)
*C10N 30/06* (2006.01)
*C10N 40/18* (2006.01)
*C10N 50/00* (2006.01)

(52) U.S. Cl.
CPC ......... *C07D 303/26* (2013.01); *C07D 333/16* (2013.01); *C07D 409/12* (2013.01); *C10M 105/54* (2013.01); *C10M 107/38* (2013.01); *G11B 5/725* (2013.01); *G11B 5/733* (2013.01); *C10M 2211/04* (2013.01); *C10M 2211/0425* (2013.01); *C10M 2213/04* (2013.01); *C10M 2213/043* (2013.01); *C10N 2030/06* (2013.01); *C10N 2040/18* (2013.01); *C10N 2050/025* (2020.05)

(58) Field of Classification Search
CPC .............. C07D 409/12; C10M 105/54; C10M 107/38; C10M 2211/0425; C10M 2211/04; C10M 2213/04; C10M 2213/043; C10N 2050/025; C10N 2030/06; C10N 2040/18; G11B 5/725; G11B 5/733; G11B 5/7257
See application file for complete search history.

(56) References Cited

U.S. PATENT DOCUMENTS

| | | |
|---|---|---|
| 2004/0235685 A1 | 11/2004 | Russo et al. |
| 2010/0261039 A1 | 10/2010 | Itoh et al. |
| 2012/0225217 A1 | 9/2012 | Itoh et al. |
| 2013/0209837 A1 | 8/2013 | Sagata et al. |
| 2015/0371672 A1 | 12/2015 | Sagata |

FOREIGN PATENT DOCUMENTS

| | | |
|---|---|---|
| EP | 3 081 549 A1 | 10/2016 |
| JP | 2004-346318 A | 12/2004 |
| JP | 4632144 B2 | 2/2011 |
| JP | 2012-009090 A | 1/2012 |
| JP | 2013-163667 A | 8/2013 |
| JP | 5465454 B2 | 4/2014 |
| JP | 5613916 B2 | 10/2014 |
| JP | 5909837 B2 | 4/2016 |
| WO | 2006/011387 A1 | 2/2006 |
| WO | 2009/123043 A1 | 10/2009 |
| WO | 2015/087615 A1 | 6/2015 |

OTHER PUBLICATIONS

International Search Report for PCT/JP2017/003165 dated May 9, 2017.
"Cihai Sciences vol. I", Edited by Cihai Editorial Committee, Shanghai Lexicographical Publishing House, Aug. 30, 1980, p. 329 (3 pages total).
Office Action dated May 25, 2021 from the China National Intellectual Property Administration in CN Application No. 201780012469.9, (Partial Translation (Search Report only).

* cited by examiner

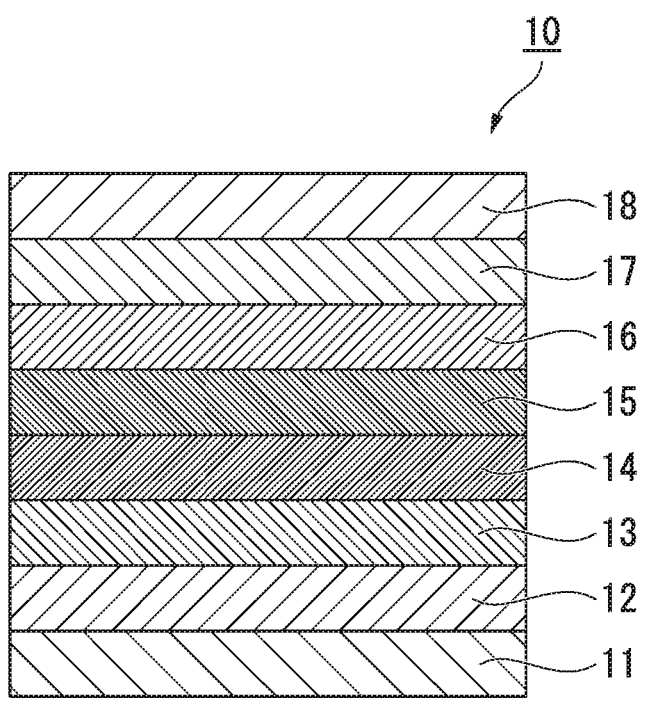

FLUORINE-CONTAINING ETHER COMPOUND, LUBRICANT FOR MAGNETIC RECORDING MEDIUM, AND MAGNETIC RECORDING MEDIUM

BACKGROUND OF THE INVENTION

Field of the Invention

The present invention relates to a fluorine-containing ether compound suitable for application as a lubricant of a magnetic recording medium, a lubricant for a magnetic recording medium including the same, and a magnetic recording medium.

This application is a National Stage of International Application No. PCT/JP2017/003165 filed Jan. 30, 2017, which claims priority to Japanese Patent Application No. 2016-047359 filed on Mar. 10, 2016, the contents of which are incorporated herein by reference.

Description of Related Art

In order to improve the recording density of magnetic recording/reproducing apparatuses, magnetic recording media suitable for high recording densities are being developed.

In the related art, there is a magnetic recording medium in which a recording layer is formed on a substrate and a protective layer of carbon or the like is formed on the recording layer. The protective layer protects the information recorded on the recording layer and improves the sliding of the magnetic head. However, it is not possible to sufficiently obtain durability of the magnetic recording medium simply by providing a protective layer on the recording layer. For this reason, in general, a lubricant is applied to the surface of the protective layer to form a lubricating layer.

As a lubricant used for forming a lubricating layer of a magnetic recording medium, for example, a lubricant was proposed containing a compound having a polar group such as a hydroxyl group at the end of a fluorine-based polymer having a repeating structure containing $CF_2$ (for example, refer to Patent Documents 1 to 3).

For example, Patent Document 1 discloses a compound in which a substituent. which has a plurality of hydroxyl groups at both ends with the shortest distance between the hydroxyl groups being separated by 3 atoms or more, is arranged. In addition, Patent Document 2 discloses a fluoropolyether compound having an aromatic group at one end and a hydroxyl group at the other end. In addition, Patent Document 3 discloses a compound having a perfluoropolyether main chain and having an aromatic group and a hydroxyl group at the end of the molecule, in which the aromatic group and the hydroxyl group are bonded to different carbon atoms.

PRIOR ART DOCUMENT

Patent Document

[Patent Document 1] Japanese Patent No. 4632144
[Patent Document 2] Japanese Patent No. 5909837
[Patent Document 3] Japanese Patent No. 5465454

SUMMARY OF THE INVENTION

Technical Problem

In the magnetic recording/reproducing apparatuses, there is a demand to further reduce the floating height of the magnetic head. For this reason, it is required to further reduce the thickness of the lubricating layer in the magnetic recording medium.

However, generally, when the thickness of the lubricating layer is thinned, the coverage of the lubricating layer is decreased, and chemical resistance and wear resistance of the magnetic recording medium tend to be decreased.

The present invention has been made in view of the above circumstances, and it is an object of the present invention to provide a fluorine-containing ether compound suitable as a material for a lubricant for a magnetic recording medium capable of forming a lubricating layer capable of providing excellent chemical resistance and wear resistance even when the thickness is thin.

In addition, the present invention has an object of providing a lubricant for a magnetic recording medium including the fluorine-containing ether compound of the present invention.

In addition, the present invention has an object of providing a magnetic recording medium having a lubricating layer including the fluorine-containing ether compound of the present invention and having excellent reliability and durability.

Solution to Problem

The present inventors conducted intensive studies to solve the problems described above.

As a result, the present inventors found that a fluorine-containing ether compound may be used, in which, at one end of a perfluoropolyether chain, an end group including an organic group having at least one double bond or triple bond is arranged via a divalent linking group bonded by etheric oxygen, while, at the other end of the perfluoropolyether chain, an end group including two or three polar groups, in which each polar group is bonded to a different carbon atom and the carbon atoms bonded to the polar groups are bonded via a linking group including carbon atoms not bonded to polar groups, is arranged, thereby arriving at the present invention.

That is, the present invention relates to the following items.

[1] A fluorine-containing ether compound represented by Formula (1),

(In Formula (1), $R^1$ is an end group including an organic group having at least one double bond or triple bond, $R^2$ is a divalent linking group bonded to $R^1$ by etheric oxygen, $R^3$ is a perfluoropolyether chain, $R^4$ is an end group having two or three polar groups with each polar group being bonded to different carbon atoms, and the carbon atoms, to which the polar groups are bonded, being bonded to each other via a linking group including carbon atoms to which the polar groups are not bonded.)

[2] The fluorine-containing ether compound according to [1], in which the polar groups of $R^4$ in Formula (1) are hydroxyl groups.

[3] The fluorine-containing ether compound according to [1] or [2], in which $R^4$ in Formula (1) is an end group of any one of Formulas (2-1) to (2-4).

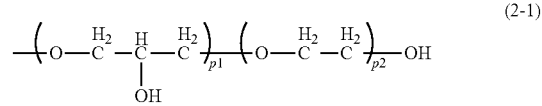

(In Formula (2-1), p1 represents 1 to 2, and p2 represents 1 to 5.)

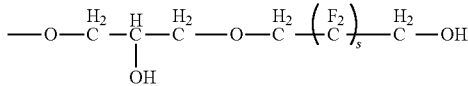
(2-2)

(In Formula (2-2), s represents 2 to 5.)

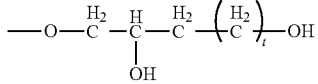
(2-3)

(In Formula (2-3), t represents 1 to 5.)

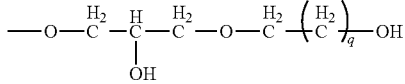
(2-4)

(In Formula (2-4), q represents 2 to 5.)

[4] The fluorine-containing ether compound according to any one of [1] to [3], in which $R^3$ in Formula (1) is represented by Formula (3).

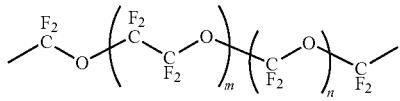
(3)

(In Formula (3), m represents 1 to 30, and n represents 0 to 30.)

[5] The fluorine-containing ether compound according to any one of [1] to [3], in which $R^3$ in Formula (1) is represented by Formula (4) or Formula (5).

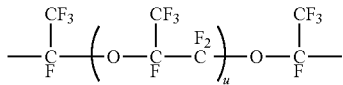
(4)

(In Formula (4), u represents 1 to 30.)

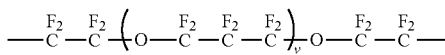
(5)

(In Formula (5), v represents 1 to 30.)

[6] The fluorine-containing ether compound according to any one of [1] to [5], in which $R^1$ in Formula (1) is any one of an end group including an aromatic ring, an end group including a heterocyclic ring, an end group including an alkenyl group, and an end group including an alkynyl group.

[7] The fluorine-containing ether compound according to any one of [1] to [6], in which $R^2$ in Formula (1) is represented by —O— or Formula (6)

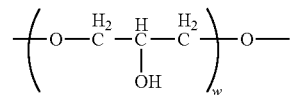
(6)

(In Formula (6), w represents 1 to 4.)

[8] The fluorine-containing ether compound according to any one of [1] to [7], in which $R^4$ in Formula (1) includes three polar groups.

[9] The fluorine-containing ether compound according to any one of [1] to [8], having a number average molecular weight in a range of 500 to 10,000.

[10] A lubricant for a magnetic recording medium including the fluorine-containing ether compound according to any one of [1] to [9].

[11] A magnetic recording medium including at least a magnetic layer, a protective layer, and a lubricating layer, which are sequentially provided on a substrate, in which the lubricating layer includes the fluorine-containing ether compound according to any one of [1] to [9].

[12] The magnetic recording medium according to [11], in which the average thickness of the lubricating layer is 0.5 nm to 3 nm.

Effect of the Invention

The fluorine-containing ether compound of the present invention is a compound represented by Formula (1) and is suitable as a material for a lubricant for a magnetic recording medium.

Since the lubricant for a magnetic recording medium of the present invention includes the fluorine-containing ether compound of the present invention, it is possible to form a lubricating layer capable of obtaining excellent chemical resistance and wear resistance even when the thickness thereof is thin.

Since the magnetic recording medium of the present invention is provided with a lubricating layer having excellent chemical resistance and wear resistance, the magnetic recording medium has excellent reliability and durability.

BRIEF DESCRIPTION OF THE DRAWINGS

FIG. 1 is a schematic cross-sectional view showing one embodiment of a magnetic recording medium of the present invention.

DETAILED DESCRIPTION OF THE INVENTION

A detailed description will be given below of the fluorine-containing ether compound, the lubricant for a magnetic recording medium, and the magnetic recording medium of the present invention. The present invention is not limited only to the embodiments described below.

[Fluorine-Containing Ether Compound]

The fluorine-containing ether compound of the present embodiment is represented by Formula (1),

(1).

(In Formula (1), $R^1$ is an end group including an organic group having at least one double bond or triple bond, $R^2$ is a divalent linking group bonded to $R^1$ by etheric oxygen, $R^3$ is a perfluoropolyether chain, $R^4$ is an end group having two or three polar groups with each polar group being bonded to different carbon atoms, and the carbon atoms, to which the polar groups are bonded, being bonded to each other via a linking group including carbon atoms to which the polar groups are not bonded.)

Here, a description will be given of the reasons why excellent chemical resistance and wear resistance are obtained even when the thickness is thin in a case where a lubricating layer was formed on the protective layer of the magnetic recording medium using a lubricant for a magnetic recording medium including the fluorine-containing ether compound of the present embodiment (may be abbreviated below as "lubricant").

As shown in Formula (1), in the fluorine-containing ether compound of the present embodiment, at one end of a perfluoropolyether chain (may be abbreviated below as "PFPE chain") represented by $R^3$, an end group including an organic group having at least one double bond or triple bond and represented by $R^1$ is arranged via a divalent linking group bonded to $R^1$ by etheric oxygen and represented by $R^1$. In the lubricating layer including the fluorine-containing ether compound of the present embodiment, the PFPE chain covers the surface of the protective layer and reduces frictional force between the magnetic head and the protective layer. In addition, the end group including an organic group having at least one double bond or triple bond and represented by $R^1$ improves the wear resistance of the lubricating layer including the fluorine-containing ether compound of the present embodiment due to intermolecular interaction of the organic group having at least one double bond or triple bond and/or interaction between the organic group and the protective layer. Accordingly, the lubricating layer including the fluorine-containing ether compound of the present embodiment obtains excellent wear resistance, for example, in comparison with a lubricating layer including a fluorine-containing ether compound in which a hydroxyl group is arranged instead of an end group represented by $R^1$.

In addition, at the end (other end) opposite to $R^2$ in the PFPE chain represented by $R^3$ in Formula (1), the end group represented by $R^4$ is arranged. The end group represented by $R^4$ includes two or three polar groups. The two or three polar groups included in the end group represented by $R^4$ adhere the fluorine-containing ether compound and the protective layer to each other in the lubricating layer including the fluorine-containing ether compound of the present embodiment so as to improve the chemical resistance and wear resistance and to suppress pick-up.

In addition, in the lubricating layer described above, the two or three polar groups included in the end group represented by $R^4$ are bonded to different carbon atoms, and the carbon atoms to which the polar groups are bonded are bonded to each other via a linking group including carbon atoms not bonded to polar groups. In the fluorine-containing ether compound having an end group represented by $R^4$, aggregation does not easily occur, for example, in comparison with a fluorine-containing ether compound in which two polar groups included in the end group are bonded to different carbon atoms, and carbon atoms bonded to polar groups are bonded to each other. Therefore, in the lubricating layer including the fluorine-containing ether compound of the present embodiment, it is possible to prevent the fluorine-containing ether compound, which is present without being adhered (adsorbed) to the protective layer, from aggregating and attaching to the magnetic head as a foreign substance (smear) and pick-up is suppressed. In addition, since the fluorine-containing ether compounds are not easily aggregated, the fluorine-containing ether compound in the lubricating layer is easily arranged in a state of spreading and extending in the plane direction on the protective layer. Therefore, it is estimated that the lubricant including the fluorine-containing ether compound described above is able to form a lubricating layer having excellent chemical resistance which is able to coat the surface of the protective layer with a high coverage even if the thickness thereof is thin.

In the fluorine-containing ether compound of the present embodiment represented by Formula (1), $R^4$ is an end group having two or three polar groups with each polar group being bonded to different carbon atoms, and the carbon atoms, to which the polar groups are bonded, being bonded to each other via a linking group including carbon atoms to which the polar groups are not bonded. The end group represented by $R^4$ contributes to the adhesion between the protective layer coated with the lubricant including the fluorine-containing ether compound of the present embodiment and the lubricating layer formed by coating the lubricant. $R^4$ in Formula (1) is able to be appropriately selected according to the performance required for a lubricant including a fluorine-containing ether compound.

In addition, the fluorine-containing ether compound of the present embodiment represented by Formula (1) is an asymmetric compound having different end groups ($R^1$, $R^4$) bonded to both ends of the PFPE chain ($R^3$). In comparison with a compound in which the same end groups are bonded to both ends, excellent chemical resistance and wear resistance are obtained in a compound in which different end groups are bonded to both ends due to the synergistic effect of the end groups ($R^1$, $R^4$) having different functions which are respectively bonded to the molecular ends.

Examples of the polar group in $R^1$ include a hydroxyl group, an amino group, a carboxyl group, a thiol group, and the like. Here, the ether bond (—O—) is not included in the polar group in $R^4$.

The polar groups in the end group of $R^1$ including two or three polar groups are preferably hydroxyl groups since it is possible to obtain a lubricating layer including a fluorine-containing ether compound having good adhesion to the protective layer.

$R^4$ in Formula (1) is preferably any one of the end groups of Formulas (2-1) to (2-4). This $R^4$ contributes to high adhesion and coverage between the protective layer to be coated with the lubricant including the fluorine-containing ether compound of the present embodiment and the lubricating layer formed by coating the lubricant.

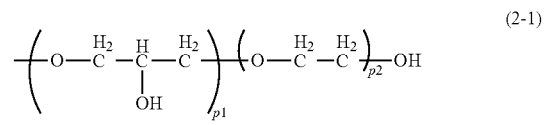

(2-1)

(In Formula (2-1), p1 represents 1 to 2, and p2 represents 1 to 5.)

In Formula (2-1), p1 is 1 to 2.

In Formula (2-1), in a case where p2 is 1 to 5, it is possible to form a lubricating layer with high coverage in which the distance between the hydroxyl groups in the end group represented by Formula (2-1) becomes appropriate and the adhesion to the protective layer is excellent. p2 is preferably 1 to 2, and most preferably 1.

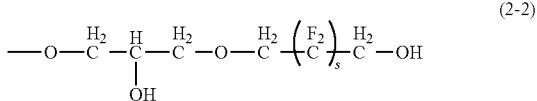
(2-2)

(In Formula (2-2), s represents 2 to 5.)

In Formula (2-2), in a case where s is 2 to 5, it is possible to form a lubricating layer with high coverage in which the distance between the hydroxyl group on the $R^3$ side and the end hydroxyl group is appropriate, and the adhesion to the protective layer is excellent. s is preferably 2 to 3, and most preferably 2.

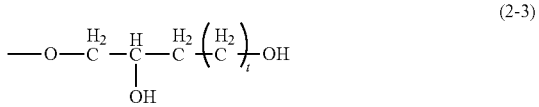
(2-3)

(In Formula (2-3), t represents 1 to 5.)

In Formula (2-3), in a case where t is 1 to 5, it is possible to form a lubricating layer with high coverage in which the distance between the hydroxyl group on the $R^3$ side and the end hydroxyl group is appropriate, and the adhesion to the protective layer is excellent. t is preferably 1 to 2, and most preferably 1.

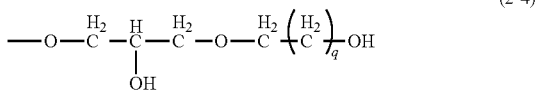
(2-4)

(In Formula (2-4), q represents 2 to 5.)

In Formula (2-4), in a case where q is 2 to 5, it is possible to form a lubricating layer with high coverage in which the distance between the hydroxyl group on the $R^3$ side and the end hydroxyl group is appropriate, and the adhesion to the protective layer is excellent. q is preferably 2 to 3.

In Formula (1). $R^1$ is a perfluoropolyether chain (PFPE chain). In the case where a lubricant including a fluorine-containing ether compound is coated on the protective layer to form a lubricating layer, the PFPE chain covers the surface of the protective layer and imparts lubricity to the lubricating layer to reduce the frictional force between the magnetic head and the protective layer.

$R^3$ is not particularly limited and is able to be appropriately selected according to the performance or the like required for a lubricant including a fluorine-containing ether compound.

In Formula (1), $R^3$ is preferably the PFPE chain represented by Formula (3), since synthesis of the fluorine-containing ether compound is easy.

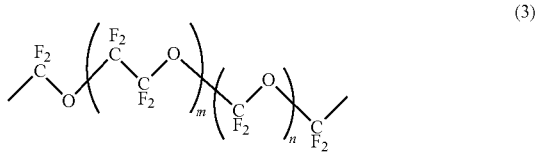
(3)

(In Formula (3), m represents 1 to 30, and n represents 0 to 30.)

In Formula (3), the order of arrangement of ($CF_2$—$CF_2$—O) and ($CF_2$—O) of which each is a repeating unit is not particularly limited. The number m of ($CF_2$—$CF_2$—O) and the number n of ($CF_2$—O) in Formula (3) may be the same or different. Formula (3) may include any one of random copolymers, block copolymers, and alternating copolymers formed of the monomer units ($CF_2$—$CF_2$—O) and ($CF_2$—O).

In a case where $R^3$ in Formula (1) is Formula (3), m is 1 to 30, preferably 1 to 20, and more preferably 1 to 15.

In a case where $R^3$ in Formula (1) is Formula (3), n is 0 to 30, preferably 0 to 20, and more preferably 0 to 15. In addition, in a case where n is 0, m is preferably 1 to 17.

In Formula (1), $R^3$ may be Formula (4) or Formula (5).

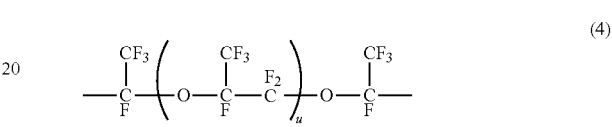
(4)

(In Formula (4), u represents 1 to 30.)

In Formula (4), in a case where u is 1 to 30, it is easy for the number average molecular weight of the fluorine-containing ether compound of the present embodiment to be in a preferable range. u is preferably 3 to 20, and more preferably 4 to 10.

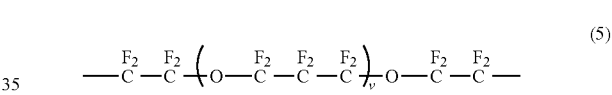
(5)

(In Formula (5), v represents 1 to 30.)

In Formula (5), in a case where v is 1 to 30, it is easy for the number average molecular weight of the fluorine-containing ether compound of the present embodiment to be in a preferable range. v is preferably 3 to 20, and more preferably 4 to 10.

In a case where $R^3$ in Formula (1) is any one of the Formula (3) to Formula (5), synthesis of the fluorine-containing ether compound is easy, which is preferable. In addition, in a case where $R^3$ in Formula (1) is any one of the Formula (3) to Formula (5), the ratio of the number of oxygen atoms (the number of ether bonds (—O—)) with respect to the number of carbon atoms in the perfluoropolyether chain is appropriate. For this reason, a fluorine-containing ether compound having appropriate hardness is obtained. Therefore, the fluorine-containing ether compound coated on the protective layer does not easily aggregate on the protective layer, and it is possible to form a lubricating layer having an even thin thickness with a sufficient coverage. In addition, a case where $R^3$ in Formula (1) is Formula (3) is more preferable since the raw materials are easily obtained.

$R^1$ in Formula (1) is an end group including an organic group having at least one double bond or triple bond. $R^1$ is preferably any one of an end group including an aromatic ring, an end group including a heterocyclic ring, an end group including an alkenyl group, or an end group including an alkynyl group.

Specific examples of the end group including an organic group having at least one double bond or triple bond used as $R^1$ include a phenyl group, a methoxyphenyl group, a naphthyl group, a benzyl group, a methoxybenzyl group, a naphthylmethyl group, a methoxynaphthyl group, a pyrrolyl group, a pyrazolyl group, a methylpyrazolylmethyl group, an imidazolyl group, a furyl group, a furfuryl group, an oxazolyl group, an isoxazolyl group, a thienyl group, a thienylethyl group, a thiazolyl group, a methylthiazolylethyl group, an isothiazolyl group, a pyridyl group, a pyrimidinyl group, a pyridazinyl group, a pyrazinyl group, an indolinyl group, a benzofuranyl group, a benzothienyl group, a benzoimidazolyl group, a benzoxazolyl group, a benzothiazolyl group, a benzopyrazolyl group, a benzoisoxazolyl group, a benzoisothiazolyl group, a quinolyl group, an isoquinolyl group, a quinazolinyl group, a quinoxalinyl group, a phthalazinyl group, or a cinnolinyl group, a vinyl group, an allyl group, a butenyl group, a propynyl group, a propargyl group, a butynyl group, a methylbutynyl group, a pentynyl group, a methylpentynyl group, a hexynyl group, cyanoethyl group, and the like. These end groups including an organic group having at least one double bond or triple bond may have a substituent such as an alkyl group, an alkoxy group, a hydroxyl group, a thiol group, a carboxyl group, a carbonyl group, and an amino group.

$R^1$ is particularly preferably any one of a phenyl group, a p-methoxyphenyl group, a naphthyl group, a p-methoxybenzyl group, a thienyl ethyl group, a methylpyrazolyl methyl group, a methylthiazolyl ethyl group, a furfuryl group, a butenyl group, an allyl group, a propargyl group, a benzyl group, and a naphthyl methyl group. When $R^1$ is one of these preferable examples, a fluorine-containing ether compound able to form a lubricating layer having better wear resistance is obtained.

$R^2$ in Formula (1) is a divalent linking group bonded to $R^1$ by etheric oxygen. The divalent linking group represented by $R^2$ is not particularly limited as long as the divalent linking group is bonded to $R^1$ by etheric oxygen and is able to be appropriately selected depending on the performance or the like required for a lubricant including a fluorine-containing ether compound.

In order to improve the adhesion between the protective layer on which the lubricant including the fluorine-containing ether compound is coated and the lubricating layer formed by coating the lubricant, the divalent linking group represented by $R^2$ preferably has one or more polar groups. Examples of the polar groups included in the linking group include a hydroxyl group, a carboxyl group, an amino group, an aminocarboxyl group, and the like, and a hydroxyl group is preferable. When the divalent linking group represented by $R^2$ includes at least one hydroxyl group, in particular, in a case where the protective layer coated with the lubricant is formed of carbon or carbon including nitrogen, the adhesion between the protective layer and the lubricating layer including the fluorine-containing ether compound is further improved.

In a case where the divalent linking group represented by $R^2$ has one or more polar groups, the number of polar groups of the linking group is not particularly limited and may be one or there may be a plurality of groups. In order to prevent the number average molecular weight of the fluorine-containing ether compound from becoming excessively large, the number of polar groups of the linking group is preferably 4 or less.

In Formula (1), the divalent linking group represented by $R^2$ preferably has 1 to 20 carbon atoms. When the number of carbon atoms is 20 or less, it is possible to prevent the number average molecular weight of the fluorine-containing ether compound from becoming excessively large. The number of carbon atoms in the linking group is more preferably 3 to 12.

Specifically, $R^2$ in Formula (1) is preferably represented by Formula (6).

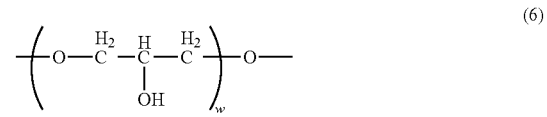

(In Formula (6), w represents 1 to 4.)

When w is 1 or more in Formula (6), the divalent linking group represented by $R^2$ including one or more hydroxyl groups further improves the adhesion between the protective layer and the lubricating layer, which is preferable. In addition, in a case where w is 4 or less, it is possible to prevent the number average molecular weight of the fluorine-containing ether compound from becoming excessively large, which is preferable. w is more preferably 1 to 2.

$R^2$ in Formula (1) may be —O— since synthesis of the fluorine-containing ether compound is easy.

Specifically, the fluorine-containing ether compound of the present embodiment is preferably any compound represented by Formulas (A) to (AC). Since the number of repetitions of m, n, and the like in Formulas (A) to (AC) is a value indicating the average value, the number is not necessarily an integer.

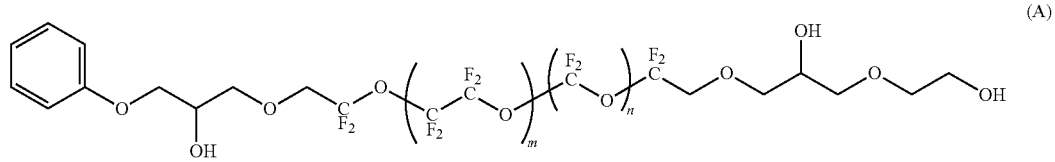

(In Formula (A), m represents 1 to 30, and n represents 0 to 30.)
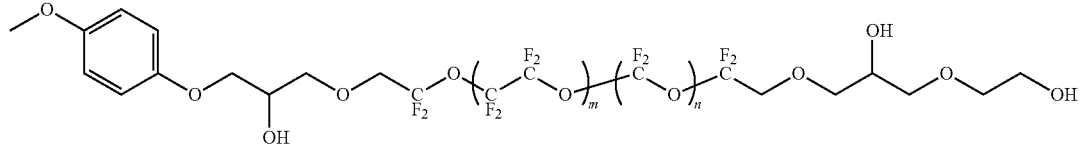
(B)
(In Formula (B), m represents 1 to 30, and n represents 0 to 30.)
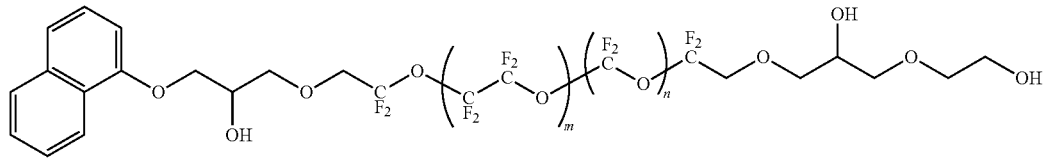
(C)
(In Formula (C), m represents 1 to 30, and n represents 0 to 30.)
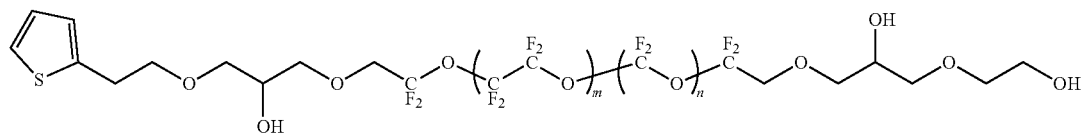
(D)
(In Formula (D), m represents 1 to 30, and n represents 0 to 30.)
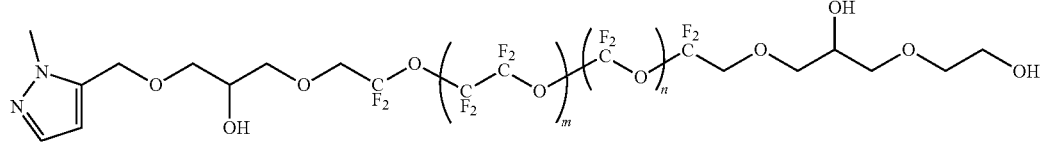
(E)
(In Formula (E), m represents 1 to 30, and n represents 0 to 30.)
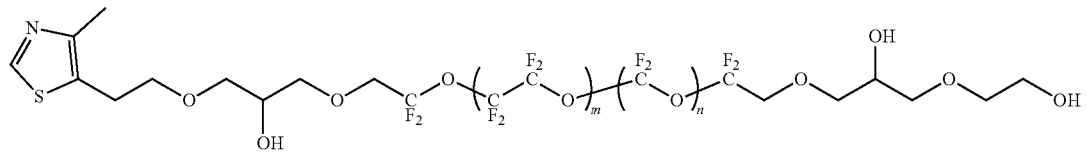
(F)

(In Formula (F), m represents 1 to 30, and n represents 0 to 30.)
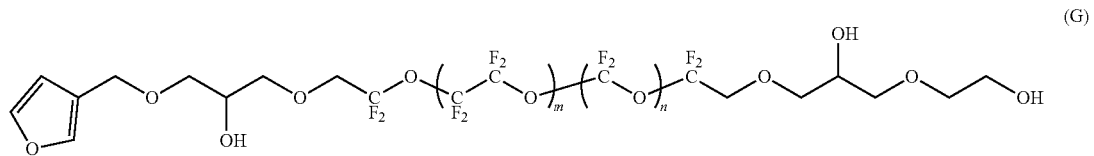
(G)
(In Formula (G), m represents 1 to 30, and n represents 0 to 30.)
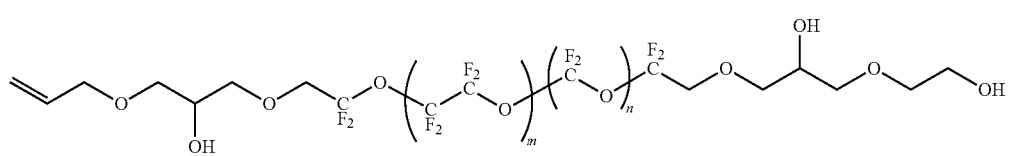
(H)
(In Formula (H), m represents 1 to 30, and n represents 0 to 30.)
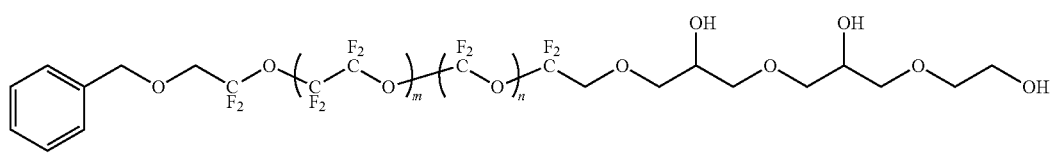
(I)
(In Formula (I), m represents 1 to 30, and n represents 0 to 30.)
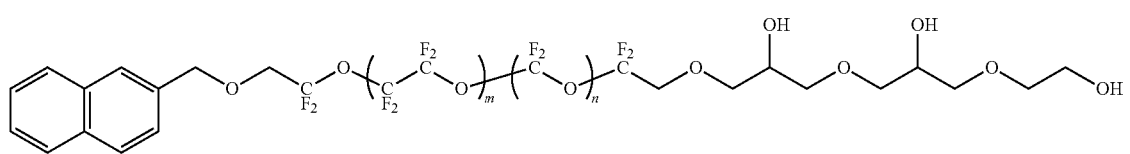
(J)
(In Formula (J), m represents 1 to 30, and n represents 0 to 30.)
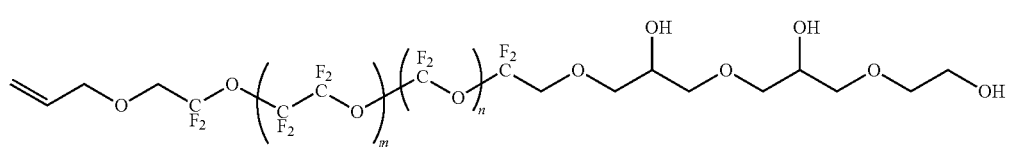
(K)

(In Formula (K), m represents 1 to 30, and n represents 0 to 30.)
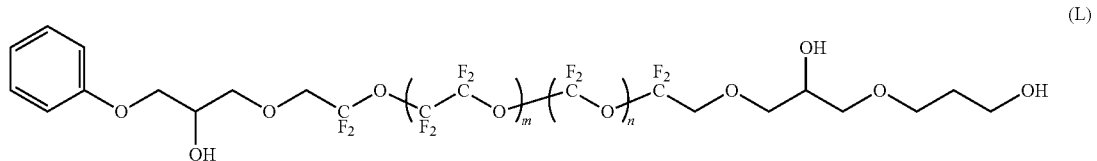
(In Formula (L), m represents 1 to 30, and n represents 0 to 30.)
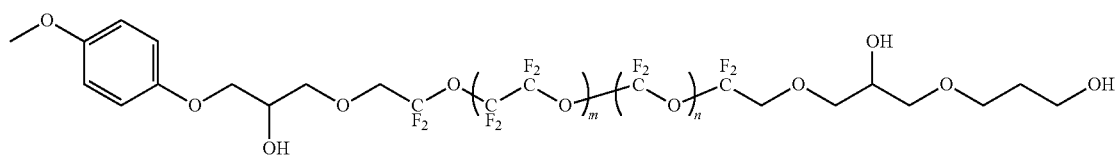
(In Formula (M), m represents 1 to 30, and n represents 0 to 30.)
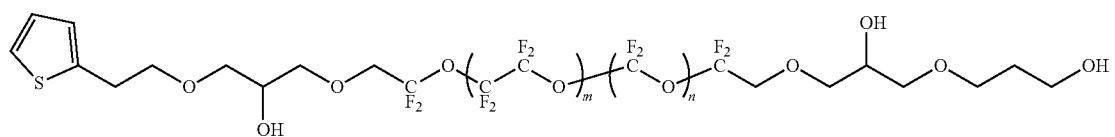
(In Formula (N), m represents 1 to 30, and n represents 0 to 30.)
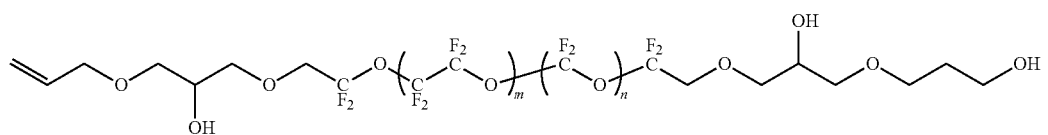
(In Formula (O), m represents 1 to 30, and n represents 0 to 30.)
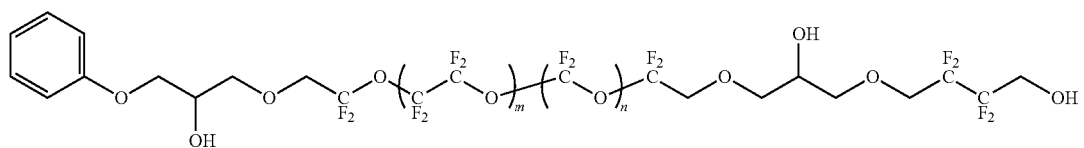

(In Formula (P), m represents 1 to 30, and n represents 0 to 30.)
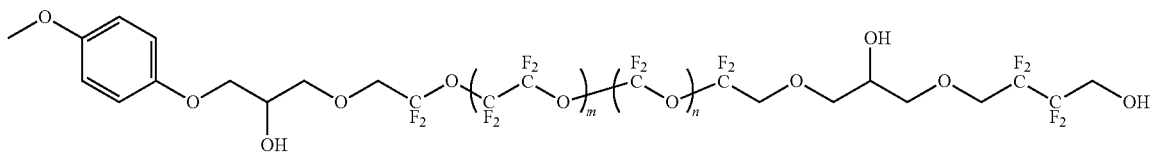
(Q)
(In Formula (Q), m represents 1 to 30, and n represents 0 to 30.)
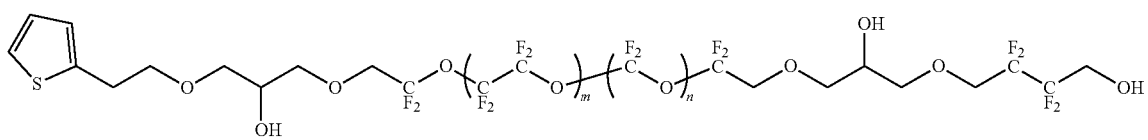
(R)
(In Formula (R), m represents 1 to 30, and n represents 0 to 30.)
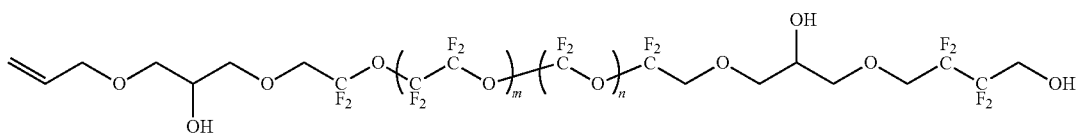
(S)
(In Formula (S), m represents 1 to 30, and n represents 0 to 30.)
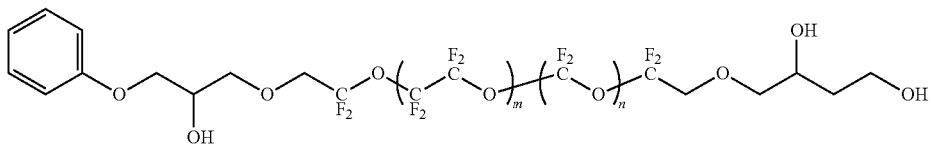
(T)
(In Formula (T), m represents 1 to 30, and n represents 0 to 30.)
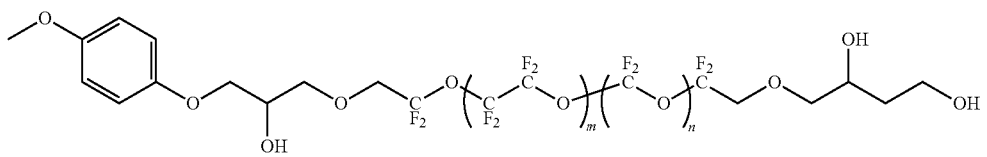
(U)

(In Formula (U), m represents 1 to 30, and n represents 0 to 30.)
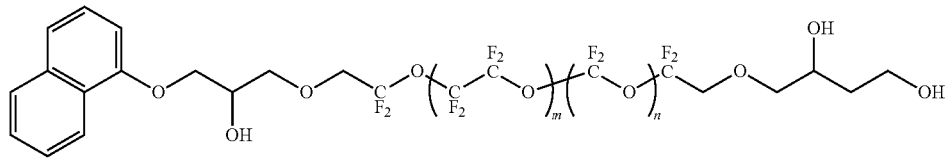
(V)
(In Formula (V), m represents 1 to 30, and n represents 0 to 30.)
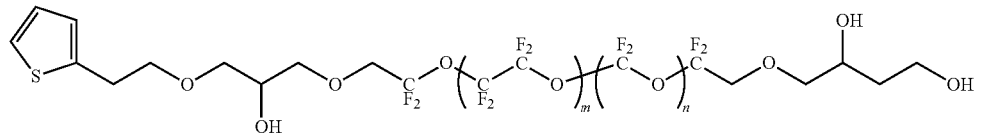
(W)
(In Formula (W), m represents 1 to 30, and n represents 0 to 30.)
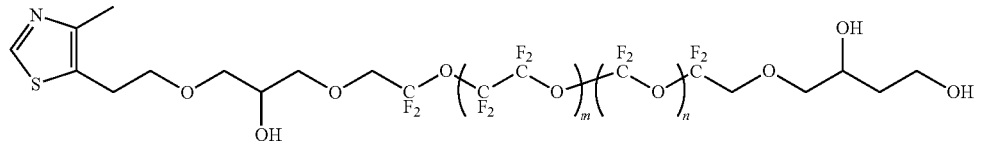
(X)
(In Formula (X), m represents 1 to 30, and n represents 0 to 30.)
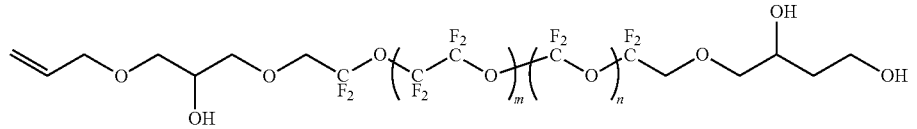
(Y)
(In Formula (Y), m represents 1 to 30, and n represents 0 to 30.)
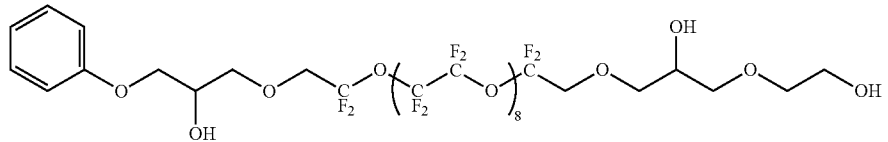
(Z)
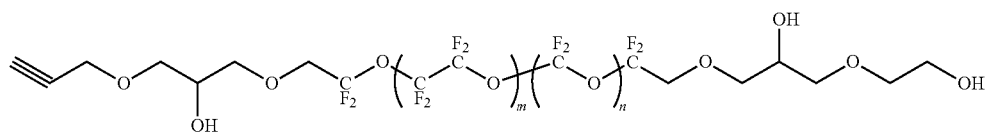
(AB)

(AC)

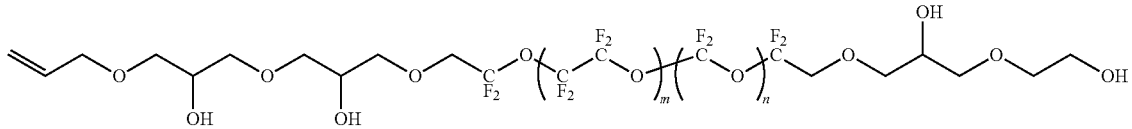

(In Formula (AB), m represents 1 to 30, and n represents 0 to 30.)

(In Formula (AC), m represents 1 to 30, and n represents 0 to 30.)

When the compound represented by Formula (1) is any one of the compounds represented by Formulas (A) to (AC), raw materials are readily available and it is possible to form a lubricating layer having excellent chemical resistance and wear resistance even when the thickness thereof is thin, which is preferable.

The fluorine-containing ether compound of the present embodiment preferably has a number average molecular weight in a range of 500 to 10,000. When the number average molecular weight is 500 or more, the lubricant including the fluorine-containing ether compound of the present embodiment does not easily evaporate and it is possible to prevent the lubricant from evaporating and being transferred and stuck to the magnetic head. The number average molecular weight of the fluorine-containing ether compound is more preferably 1000 or more. In addition, when the number average molecular weight is 10000 or less, the viscosity of the fluorine-containing ether compound is appropriate, and by coating a lubricant including the fluorinated ether compound, it is possible to easily form a thin lubricating layer. The number average molecular weight of the fluorine-containing ether compound is preferably 3000 or less in order to have a viscosity allowing easy handling in a case of being applied to a lubricant.

The number average molecular weight is a value measured by $^1$H-NMR and $^{19}$F-NMR by AVANCE III 400 manufactured by Bruker BioSpin. In the measurement of NMR (nuclear magnetic resonance), the sample was diluted in a hexafluorobenzene/d-acetone (4/lv/v) solvent and used for measurement. On the basis of $^{19}$F-NMR chemical shift, the peak of hexafluorobenzene was −164.7 ppm, and on the basis of $^1$H-NMR chemical shift, the peak of acetone was 2.2 ppm.

[Manufacturing Method]

The method for manufacturing the fluorine-containing ether compound of the present embodiment is not particularly limited, and manufacturing is possible by a manufacturing method known in the related art. It is possible to manufacture the fluorine-containing ether compound of the present embodiment, for example, using the manufacturing method described below.

First, a fluorine compound having hydroxymethyl groups (—CH$_2$OH) arranged at both ends of a perfluoropolyether chain corresponding to R$^3$ in Formula (1) is prepared.

Subsequently, the hydroxyl group of the hydroxymethyl group arranged at one end of the fluorine compound is substituted with an end group formed of R$^1$—R$^2$— in Formula (1) (first reaction). Thereafter, the hydroxyl group of the hydroxymethyl group arranged at the other end is substituted with an end group formed of —R$^4$ in Formula (1) (second reaction).

It is possible to carry out the first reaction and the second reaction by a method known in the related art and it is possible to appropriately determine the method depending on the type of R$^1$, R$^2$, and R$^1$ in Formula (1), or the like. In addition, either of the first reaction and the second reaction may be performed first.

By the above method, the compound represented by Formula (1) is obtained.

In the present embodiment, in a case of manufacturing a fluorine-containing ether compound in which R$^2$ is represented by Formula (6), the fluorine-containing ether compound is preferably manufactured using an epoxy compound. It is possible to synthesize the epoxy compound using an alcohol having a structure corresponding to the end group represented by R$^1$ of the fluorine-containing ether compound to be manufactured, and epichlorohydrin or epibromohydrin.

Specifically, for example, in the case of the epoxy compound represented by Formula (12) described below, it is possible to obtain the epoxy compound by reacting thiopheneethanol and epichlorohydrin in the presence of a base.

The fluorine-containing ether compound of the present embodiment is a compound represented by Formula (1). Therefore, when a lubricating layer is formed on the protective layer using the lubricant including the fluorine-containing ether compound, the surface of the protective layer is covered with the PFPE chain represented by R$^3$ in Formula (1), and the frictional force between the magnetic head and the protective layer is reduced. In addition, in the lubricating layer formed using the lubricant including the fluorine-containing ether compound of the present embodiment, it is possible to obtain excellent wear resistance due to the intermolecular interaction in the end group represented by R$^1$ and/or the interaction between the end group and the protective layer.

In addition, in the fluorine-containing ether compound of the present embodiment, the PFPE chain is adhered to the protective layer by bonding between two or three polar groups of R$^4$ linked to the PFPE chain and the protective layer. Therefore, according to the fluorine-containing ether compound of the present embodiment, it is possible to obtain a lubricating layer in which the lubricating layer and the protective layer are strongly bonded, and which has excellent chemical resistance and wear resistance.

[Lubricant for Magnetic Recording Medium]

The lubricant for a magnetic recording medium of the present embodiment includes a fluorine-containing ether compound represented by Formula (1).

As long as the lubricant of the present embodiment is in a range which does not impair characteristics due to the inclusion of the fluorine-containing ether compound represented by Formula (1), it is possible to use known materials for a lubricant in a mixture as necessary.

Specific examples of known materials include FOMBLIN (registered trademark) ZDIAC, FOMBLIN ZDEAL, FOMBLIN AM-2001 (manufactured by Solvay Solexis Inc.), Moresco A 20 H (manufactured by Moresco Corp.), and the like.

A known material used by mixing with the lubricant of the present embodiment preferably has a number-average molecular weight of 1,000 to 10,000.

In the case where the lubricant of the present embodiment includes another material of the fluorine-containing ether compound represented by Formula (1), the content of the fluorine-containing ether compound represented by Formula (1) in the lubricant of the present embodiment is preferably 50% by mass or more, and more preferably 70% by mass or more.

Since the lubricant of the present embodiment includes the fluorine-containing ether compound represented by Formula (1), even when the thickness thereof is thin, it is possible to cover the surface of the protective layer with a high coverage and it is possible to form a lubricating layer with excellent adhesion to the protective layer. Therefore, according to the lubricant of the present embodiment, even if the thickness thereof is thin, it is possible to obtain a lubricating layer having excellent chemical resistance and wear resistance.

In addition, since the lubricant of the present embodiment includes the fluorine-containing ether compound represented by Formula (1), the fluorine-containing ether compound in the lubricant layer which is present without adhering (adsorbing) to the protective layer does not easily aggregate. Therefore, it is possible to prevent the fluorine-containing ether compound from aggregating and attaching to the magnetic head as a foreign substance (smear), and pick-up is suppressed.

In addition, since the lubricant of the present embodiment includes the fluorine-containing ether compound represented by Formula (1), it is possible to obtain a lubricating layer having excellent wear resistance due to the intermolecular interaction in the organic group having at least one double bond or triple bond in the end group represented by $R^1$ and/or interaction between the organic group and the protective layer.

[Magnetic Recording Medium]

FIG. 1 is a schematic cross-sectional view showing one embodiment of the magnetic recording medium of the present invention.

The magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

[Substrate]

As the substrate 11, for example, it is possible to use a nonmagnetic substrate or the like in which a layer formed of NiP or NiP alloy is formed on a substrate formed of a metal or an alloy material such as Al or an Al alloy.

In addition, as the substrate 11, a nonmagnetic substrate formed of a non-metallic material such as glass, ceramics, silicon, silicon carbide, carbon, resin, or the like may be used, or a nonmagnetic substrate in which a layer of an NiP or NiP alloy is formed on a base formed of these non-metal materials may be used.

[Adhesive Layer]

The adhesive layer 12 prevents the progress of corrosion of the substrate 11 in a case where the substrate 11 and the soft magnetic layer 13 provided on the adhesive layer 12 are arranged in contact with each other.

It is possible to appropriately select the material of the adhesive layer 12 from, for example, Cr, a Cr alloy, Ti, a Ti alloy, and the like. It is possible to form the adhesive layer 12 by, for example, a sputtering method.

[Soft Magnetic Layer]

It is preferable that the soft magnetic layer 13 have a structure in which a first soft magnetic layer, an intermediate layer formed of a Ru layer, and a second soft magnetic layer are laminated in order. That is, the soft magnetic layer 13 preferably has a structure in which, by interposing an intermediate layer formed of a Ru layer between two layers of soft magnetic layers, the upper and lower soft magnetic layers of the intermediate layer are bonded by anti-ferro-coupling (AFC). When the soft magnetic layer 13 has an AFC-bonded structure, it is possible to increase the resistance to external magnetic fields and the resistance to the Wide Area Tack Erasure (WATE) phenomenon, which is a problem peculiar to perpendicular magnetic recording.

It is preferable that the first soft magnetic layer and the second soft magnetic layer be layers formed of a CoFe alloy. In a case where the first soft magnetic layer and the second soft magnetic layer are layers formed of a CoFe alloy, it is possible to realize a high saturation magnetic flux density Bs (1.4 (T) or more).

In addition, it is preferable to add any one of Zr, Ta, or Nb to the CoFe alloy used for the first soft magnetic layer and the second soft magnetic layer. Due to this, amorphization of the first soft magnetic layer and the second soft magnetic layer is promoted, and it is possible to improve the orientation of the first underlayer (seed layer), and it is also possible to reduce the floating height of the magnetic head.

It is possible to form the soft magnetic layer 13 by, for example, a sputtering method.

[First Underlayer]

The first underlayer 14 is a layer for controlling the orientation and crystal size of the second underlayer 15 and the magnetic layer 16 provided thereon. The first underlayer 14 is provided to increase the components in the direction perpendicular to the substrate surface of the magnetic flux generated from the magnetic head and fix the magnetization direction of the magnetic layer 16 more firmly in the direction perpendicular to the substrate 11.

The first underlayer 14 is preferably a layer formed of a NiW alloy. In the case where the first underlayer 14 is a layer formed of a NiW alloy, other elements such as B. Mn, Ru, Pt, Mo, Ta and the like may be added to the NiW alloy as necessary.

It is possible to form the first underlayer 14 by, for example, a sputtering method.

[Second Underlayer]

The second underlayer 15 is a layer which controls the orientation of the magnetic layer 16 so as to be favorable. The second underlayer 15 is preferably a layer formed of Ru or a Ru alloy.

The second underlayer 15 may be a layer formed of one layer or a plurality of layers. In the case where the second underlayer 15 is formed of a plurality of layers, all of the layers may be formed of the same material, or at least one layer may be formed of a different material.

It is possible to form the second underlayer 15 by, for example, a sputtering method.

[Magnetic Layer]

The magnetic layer 16 is formed of a magnetic layer in which the axis of easy magnetization is perpendicular or horizontal to the substrate surface. The magnetic layer 16 is a layer including Co and Pt and may be a layer including an oxide or Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, $TiO_2$, and the like.

The magnetic layer 16 may be formed of one layer or formed of a plurality of magnetic layers formed of materials having different compositions.

For example, in the case where the magnetic layer 16 is formed of three layers of a first magnetic layer, a second magnetic layer, and a third magnetic layer, the first magnetic layer includes Co, Cr, and Pt, and preferably has a granular structure formed of a material including an oxide. As the oxide contained in the first magnetic layer, for example, it is preferable to use oxides such as Cr, Si, Ta, Al, Ti, Mg, and Co. Among these, in particular, it is possible to suitably use $TiO_2$, $Cr_2O_3$, $SiO_2$, and the like. In addition, the first magnetic layer is preferably formed of a composite oxide to which two or more oxides are added. Among these, it is possible to preferably use $Cr_2O_3$—$SiO_2$, $Cr_2O_3$—$TiO_2$, $SiO_2$—$TiO_2$, and the like.

In addition to Co, Cr, Pt and an oxide, the first magnetic layer is able to include one or more elements selected from B, Ta, Mo, Cu, Nd, W, Nb, Sm, Tb, Ru, and Re. By including one or more of the above elements, it is possible to promote miniaturization of the magnetic particles, to improve crystallinity and orientation, and to obtain recording/reproduction characteristics and thermal fluctuation characteristics suitable for higher density recording.

For the second magnetic layer, it is possible to use the same material as the first magnetic layer. It is preferable that the second magnetic layer have a granular structure.

The third magnetic layer preferably has a non-granular structure formed of a material which includes Co, Cr, and Pt and which does not include oxide. In addition to Co, Cr, and Pt, it is possible for the third magnetic layer to include one or more elements selected from B, Ta, Mo, Cu, Nd, W, Nb, Sm, Tb, Ru, Re, and Mn. Including the above elements in addition to Co, Cr and Pt in the third magnetic layer makes it possible to promote miniaturization of the magnetic particles, to improve crystallinity and orientation, and to obtain recording and reproduction characteristics and thermal fluctuation characteristics suitable for higher density recording.

In the case where the magnetic layer 16 is formed of a plurality of magnetic layers, it is preferable to provide a nonmagnetic layer between the adjacent magnetic layers. In a case where the magnetic layer 16 is formed of three layers of the first magnetic layer, the second magnetic layer, and the third magnetic layer, it is preferable to provide a nonmagnetic layer between the first magnetic layer and the second magnetic layer and between the second magnetic layer and the third magnetic layer.

By providing the nonmagnetic layer with an appropriate thickness between the adjacent magnetic layers, the magnetization reversal of each layer is facilitated, it is possible to reduce the dispersion of the magnetization reversal of the whole magnetic particles, and it is possible to further improve the S/N ratio.

For the nonmagnetic layer provided between the adjacent magnetic layers of the magnetic layer 16, it is possible to suitably use, for example, Ru, Ru alloy, CoCr alloy, CoCrX1 alloy (X1 represents one or two or more elements selected from Pt, Ta, Zr, Re, Ru, Cu, Nb, Ni, Mn, Ge, Si, O, N, W, Mo, Ti, V, Zr, and B) or the like.

It is preferable to use an alloy material including an oxide, a metal nitride, or a metal carbide for the nonmagnetic layer provided between the adjacent magnetic layers of the magnetic layer 16. Specifically, as the oxide, for example, it is possible to use $SiO_2$, $Al_2O_3$, $Ta_2O_5$, $Cr_2O_3$, MgO, $Y_2O_3$, $TiO_2$, or the like. As the metal nitride, for example, it is possible to use AlN, $Si_3N_4$, TaN, CrN, or the like. As the metal carbide, for example, it is possible to use TaC, BC, SiC, or the like.

It is possible to form the nonmagnetic layer by, for example, a sputtering method.

In order to realize a higher recording density, the magnetic layer 16 is preferably a perpendicular magnetic recording magnetic layer whose easy axis of magnetization is oriented perpendicular to the substrate surface. The magnetic layer 16 may be for in-plane magnetic recording.

The magnetic layer 16 may be formed by any method known in the related art, such as a vapor deposition method, an ion beam sputtering method, a magnetron sputtering method, or the like. The magnetic layer 16 is usually formed by a sputtering method.

[Protective Layer]

The protective layer 17 protects the magnetic layer 16. The protective layer 17 may be formed of one layer or may be formed of a plurality of layers. Examples of the material of the protective layer 17 include carbon, carbon including nitrogen, silicon carbide, and the like.

As a method for layer-forming the protective layer 17, it is possible to use a sputtering method using a target material including carbon, a chemical vapor deposition (CVD) method using a hydrocarbon material such as ethylene or toluene, an ion beam deposition (IBD) method, or the like.

[Lubricating Layer]

The lubricating layer 18 prevents contamination of the magnetic recording medium 10. In addition, the lubricating layer 18 improves the durability of the magnetic recording medium 10 by reducing the frictional force of the magnetic head of the magnetic recording/reproducing apparatus sliding on the magnetic recording medium 10.

As shown in FIG. 1, the lubricating layer 18 is formed in contact with the protective layer 17. The lubricating layer 18 is formed by coating the lubricant for the magnetic recording medium of the embodiment described above on the protective layer 17. Therefore, the lubricating layer 18 includes the fluorine-containing ether compound described above (of the present invention).

In a case where the protective layer 17 arranged under the lubricating layer 18 is formed of carbon, carbon including nitrogen, or silicon carbide, the lubricating layer 18 is bonded with a high bonding force to the fluorine-containing ether compound (of the present invention) included in the protective layer 17. As a result, even if the thickness of the lubricating layer 18 is thin, it is easy to obtain the magnetic recording medium 10 in which the surface of the protective layer 17 is covered with a high coverage, and it is possible to effectively prevent contamination of the surface of the magnetic recording medium 10.

The average thickness of the lubricating layer 18 is preferably 0.5 nm (5 Å) to 3 nm (30 Å), more preferably 0.5 nm (5 Å) to 2 nm (20 Å).

When the average thickness of the lubricating layer 18 is 0.5 nm or more, the lubricating layer 18 is formed with a uniform thickness without being formed into an island shape or mesh shape. Therefore, it is possible for the lubricating layer 18 to cover the surface of the protective layer 17 with a high coverage ratio. In addition, setting the average thickness of the lubricating layer 18 to 3 nm or less makes it possible to make the floating height of the magnetic head sufficiently small, and to increase the recording density of the magnetic recording medium 10.

In the case where the surface of the protective layer 17 is not covered with the lubricating layer 18 at a sufficiently high coverage ratio, environmental substances adsorbed on the surface of the magnetic recording medium 10 pass through the gap of the lubricating layer 18, and permeate under the lubricating layer 18. The environmental substances which permeated the lower layer of the lubricating layer 18 adsorb to and bond with the protective layer 17 to generate contaminants. Then, at the time of magnetic recording/reproduction, these contaminants (aggregated components) adhere (transfer) to the magnetic head as a smear, which damages the magnetic head and deteriorates the magnetic recording/reproducing characteristics of the magnetic recording/reproducing apparatus.

Examples of environmental substances which generate contaminants include hydrocarbons having relatively high molecular weights such as siloxane compounds (cyclic siloxanes and linear siloxanes), ionic impurities and octacosane, plasticizers such as dioctyl phthalate, and the like. Examples of the metal ions included in the ionic impurities include sodium ions, potassium ions, and the like. Examples of inorganic ions included in the ionic impurities include chlorine ions, bromine ions, nitrate ions, sulfate ions, ammonium ions, and the like. Examples of organic ions included in the ionic impurities include oxalic acid ions, formic acid ions, and the like.

[Method of Forming Lubricating Layer]

In order to form the lubricating layer 18, example methods include a method of preparing a magnetic recording medium in the manufacturing process of forming each layer up to the protective layer 17 on the substrate 11, and coating the lubricating layer-forming solution on the protective layer 17.

The lubricating layer-forming solution is obtained by diluting the lubricant for a magnetic recording medium of the embodiment described above with a solvent as necessary and setting a viscosity and a concentration suitable for the coating method. Examples of a solvent to be used for the lubricating layer-forming solution include a fluorine-based solvent such as Vertrel (registered trademark) XF (trade name, manufactured by Du Pont-Mitsui Fluorochemicals Co., Ltd.), and the like.

The method of coating the lubricating layer-forming solution is not particularly limited, and examples thereof include a spin coating method and a dipping method.

In the case of using the dipping method, for example, it is possible to use the following method. First, the substrate 11 on which each layer up to the protective layer 17 is formed is immersed in a lubricating layer-forming solution placed in an immersion tank of a dip coating apparatus. Next, the substrate 11 is pulled up from the immersion tank at a predetermined speed. Due to this, the lubricating layer-forming solution is coated on the surface of the protective layer 17 on the substrate 11.

Using the dipping method, it is possible to uniformly coat the lubricating layer-forming solution on the surface of the protective layer 17, and to form the lubricating layer 18 with a uniform thickness on the protective layer 17.

In the magnetic recording medium 10 of the present embodiment, at least a magnetic layer 16, a protective layer 17, and a lubricating layer 18 are sequentially provided on a substrate 11. In the magnetic recording medium 10 of the present embodiment, the lubricating layer 18 including the fluorine-containing ether compound described above is formed on and in contact with the protective layer 17. The lubricating layer 18 covers the surface of the protective layer 17 with a high coverage even if the thickness thereof is thin. Therefore, in the magnetic recording medium 10 of the present embodiment, environmental substances which generate contaminants such as ionic impurities are prevented from entering the gaps of the lubricating layer 18. Therefore, the magnetic recording medium 10 of the present embodiment has few contaminants present on the surface thereof. In addition, the lubricating layer 18 in the magnetic recording medium 10 of the present embodiment is less likely to produce a foreign substance (smear) and is able to suppress pick-up. In addition, the lubricating layer 18 in the magnetic recording medium 10 of the present embodiment has excellent chemical resistance and wear resistance. Therefore, the magnetic recording medium 10 of the present embodiment has excellent reliability and durability.

EXAMPLES

A more detailed description will be given below of the present invention with reference to Examples and Comparative Examples. Here, the present invention is not limited to only the following examples.

Manufacturing of Lubricant

Example 1

The compound represented by Formula (A) was manufactured by the method shown below.

Under a nitrogen gas atmosphere, 25.4 g of a compound (number average molecular weight: 1270, molecular weight distribution: 1.1) represented by $HOCH_2CF_2O(CF_2CF_2O)_q(CF_2O)_rCF_2CH_2OH$ (in the formula, q is 6 and r is 6), 1.50 g of glycidyl phenyl ether represented by Formula (7), and 10 mL of t-BuOH were added to a 100 mL eggplant-shaped flask and the mixture was stirred at room temperature until homogeneous. 0.900 g of t-BuOK was further added to this homogeneous solution, and the mixture was reacted by being stirred at 70° C. for 8 hours.

The obtained reaction product was cooled to 25° C., neutralized with 0.5 mol/L hydrochloric acid, then extracted with Vertrel XF manufactured by Du Pont-Mitsui Fluorochemicals Co., Ltd. (referred to below as Vertrel XF), and the organic layer was washed with water and dehydrated with anhydrous sodium sulfate. After filtering off the drying agent, the filtrate was concentrated, and the residue was purified by silica gel column chromatography to obtain 7.25 g of a compound represented by Formula (8).

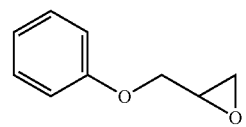

(7)

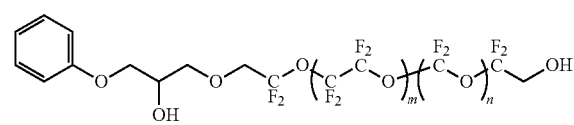

(8)

(In Formula (8), m is 6 and n is 6.)

Under a nitrogen gas atmosphere, 7.10 g of the obtained compound represented by Formula (8), 1.05 g of the compound represented by Formula (9), and 50 mL of t-BuOH were added to a 200 mL eggplant-shaped flask, and the mixture was stirred at room temperature until homogeneous. 0.187 g of t-BuOK was added to this homogeneous solution, and the reaction was carried out by being stirred at 70° C. for 16 hours.

The obtained reaction product was cooled to 25° C., neutralized with 0.1 mol/L hydrochloric acid, then extracted with Vertrel XF, and the organic layer was washed with water and dehydrated with anhydrous sodium sulfate. After filtering off the drying agent, the filtrate was concentrated.

The compound represented by Formula (9) was synthesized from ethylene glycol tert-butyl ether and epibromohydrin.

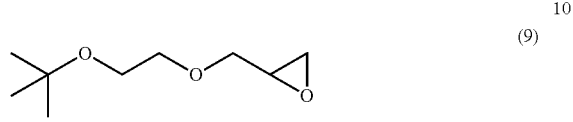

(9)

0.75 mL of water and 7.5 mL of trifluoroacetic acid were added to the obtained residue at room temperature, and the mixture was stirred at room temperature for 6 hours. Water and trifluoroacetic acid were distilled off at 35° C. or lower, 30 mL of 5% aqueous sodium bicarbonate solution was added to the obtained residue, extraction was carried out with Vertrel XF, and the organic layer was washed with water and concentrated. 5 mL of methanol and 20 mL of 1 mol/L sodium hydroxide aqueous solution were added to the obtained residue, and the mixture was stirred at room temperature for 1 hour. The methanol was distilled off, extraction was carried out with Vertrel XF, the organic layer was washed with water and dehydrated with anhydrous sodium sulfate. After filtering off the drying agent, the filtrate was concentrated, and the residue was purified by silica gel column chromatography to obtain 4.75 g of compound (A).

$^1$H-NMR measurement of the obtained compound (A) was performed, and the structure was identified based on the following results.

Compound (A): $^1$H-NMR ($C_6F_6$/$CD_3COCD_3$=4/1(V/V));
δ [ppm] 3.40 to 3.55 (3H), 3.55 to 3.90 (11H), 3.95 to 4.15 (4H), 6.80 to 7.30 (5H)

Example 2

The same operations as in Example 1 were performed except that 1.80 g of a compound represented by Formula (10) was used instead of the compound represented by Formula (7) to obtain 4.85 g of the compound (B).

$^1$H-NMR measurement of the obtained compound (B) was performed, and the structure was identified based on the following results.

Compound (B); $^1$H-NMR ($C_6F_6$/$CD_3COCD_3$=4/1 (V/V));
δ [ppm] 3.45 to 3.60 (3H), 3.60 to 4.00 (14H) 3.95 to 4.15 (4H), 6.75 to 6.85 (2H), 7.10 to 7.20 (2H)

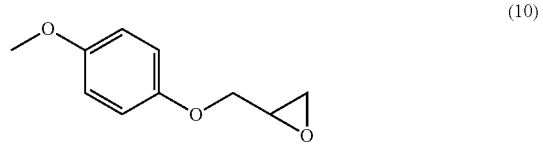

(10)

Example 3

The same operations as in Example 1 were performed except that 2.00 g of a compound represented by Formula (11) was used instead of the compound represented by Formula (7) to obtain 4.80 g of the compound (C).

The compound represented by Formula (11) was synthesized from naphthol and epichlorohydrin.

$^1$H-NMR measurement of the obtained compound (C) was performed, and the structure was identified based on the following results.

Compound (C): $^1$H-NMR ($C_6F_6$/$CD_3COCD_3$=4/1(V/V));
δ [ppm] 3.40 to 3.55 (3H), 3.60 to 3.90 (11H), 4.00 to 4.15 (4H), 7.00 to 7.70 (7H)

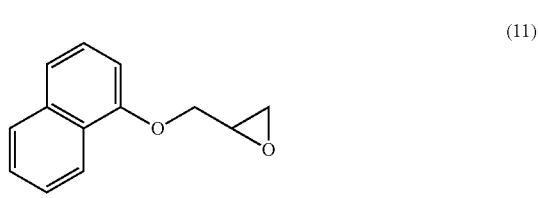 [SMILES: c1ccc2c(OCC3CO3)cccc2c1]

(11)

Example 4

The same operations as in Example 1 were performed except that 1.85 g of a compound represented by Formula (12) was used instead of the compound represented by Formula (7) to obtain 4.95 g of the compound (D).

The compound represented by Formula (12) was synthesized from thiophene ethanol and epichlorohydrin.

$^1$H-NMR measurement of the obtained compound (D) was performed, and the structure was identified based on the following results.

Compound (D): $^1$H-NMR ($C_6F_6$/$CD_3COCD_3$=4/1(V/V)):
δ [ppm]=3.15 (2H), 3.40 to 3.55 (8H), 3.60 to 3.95 (8H), 4.00 to 4.15 (4H), 6.80 (2H), 7.03 (1H)

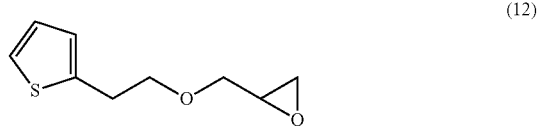 [SMILES: c1csc(CCOCC2CO2)c1]

(12)

Example 5

The same operations as in Example 1 were performed except that 1.69 g of a compound represented by Formula (13) was used instead of the compound represented by Formula (7) to obtain 4.55 g of the compound (E).

The compound represented by Formula (13) was synthesized from N-methylpyrazole methanol and epichlorohydrin.

$^1$H-NMR measurement of the obtained compound (E) was performed, and the structure was identified based on the following results.

Compound (E); $^1$H-NMR ($C_6F_6$/$CD_3COCD_3$=4/1 (V/V)):
δ [ppm]=3.40 to 3.55 (3H), 3.60 to 3.90 (16H), 4.05 to 4.20 (4H), 6.00 (1H), 7.25 (1H).

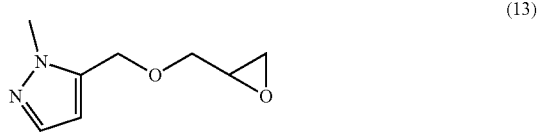

(13)

Example 6

The same operations as in Example 1 were performed except that 2.00 g of a compound represented by Formula (14) was used instead of the compound represented by Formula (7) to obtain 4.40 g of the compound (F).

The compound represented by Formula (14) was synthesized from methylthiazole ethanol and epichlorohydrin.

$^1$H-NMR measurement of the obtained compound (F) was performed, and the structure was identified based on the following results.

Compound (F); $^1$H-NMR ($C_6F_6/CD_3COCD_3$=4/1 (V/V)):
δ [ppm]=2.35 (3H), 3.00 (2H), 3.40 to 3.55 (3H), 3.60 to 3.90 (13H), 4.05 to 4.20 (4H), 8.40 (1H)

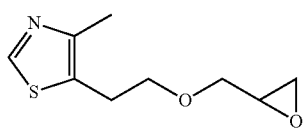

(14)

Example 7

The same operations as in Example 1 were performed except that 1.55 g of a compound represented by Formula (15) was used instead of the compound represented by Formula (7) to obtain 4.77 g of the compound (G).

The compound represented by Formula (15) was synthesized from furan methanol and epichlorohydrin.

$^1$H-NMR measurement of the obtained compound (G) was performed, and the structure was identified based on the following results.

Compound (G); 1H-NMR ($C_6F_6/CD_3COCD_3$=4/1(V/V)):
δ [ppm]=3.40 to 3.55 (3H), 3.60 to 3.95 (11H), 4.00 to 4.15 (4H), 4.45 (2H), 6.35 (1H), 7.35 (2H)

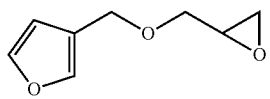

(15)

Example 8

The same operations as in Example 1 were performed except that 1.15 g of a compound represented by Formula (16) was used instead of the compound represented by Formula (7) to obtain 4.69 g of the compound (H).

$^1$H-NMR measurement of the obtained compound (H) was performed, and the structure was identified based on the following results.

Compound (H): $^1$H-NMR ($C_6F_6/CD_3COCD_3$=4/1(V/V)):
δ [ppm]=3.40 to 3.55 (3H), 3.60 to 3.95 (11H), 4.00 to 4.15 (6H), 5.15 (2H), 5.30 (1H), 5.90 to 6.00 (1H)

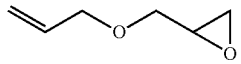

(16)

Example 9

The compound represented by Formula (I) was manufactured by the following method.

Under a nitrogen gas atmosphere, 20.0 of a compound (number average molecular weight: 997, molecular weight distribution 1.1) represented by $HOCH_2CF_2O(CF_2CF_2O)q$ $(CF_2O)rCF_2CH_2OH$ (in the formula, q is 4.5 and r is 4.5), 3.42 g of the compound represented by Formula (17), 8.29 g of potassium carbonate, and 60 mL of acetone were added to a 300 mL eggplant-shaped flask and reacted under reflux while being stirred for 24 hours.

The obtained reaction product was cooled to 25° C. and acetone was distilled off. Vertrel XF was added to the residue and the result was washed with water and dehydrated with anhydrous sodium sulfate. After filtering off the drying agent, the filtrate was concentrated and the residue was purified by silica gel column chromatography to obtain 7.52 g of a compound represented by Formula (18).

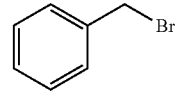

(17)

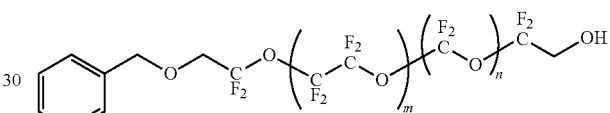

(18)

(In Formula (18), m is 4.5 and n is 4.5.)

Under a nitrogen gas atmosphere, 12 mL of ethylene glycol, 150 mL of dichloromethane, and 20.0 g of trityl chloride were added to a 500 mL eggplant-shaped flask, and the mixture was stirred until homogeneous. A solution of 20 mL of triethylamine/50 mL of dichloromethane was further added to the eggplant-shaped flask over 30 minutes under ice cooling. 0.900 g of 4-dimethylaminopyridine was further added to the eggplant-shaped flask at room temperature, and the mixture was reacted at 40° C. for 10 hours. The obtained reaction product was cooled to 25° C., washed with water, and dehydrated with anhydrous sodium sulfate. After filtering off the drying agent, the filtrate was concentrated and the residue was purified by silica gel column chromatography to obtain 19.0 g of a compound represented by Formula (19).

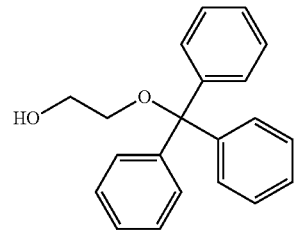

(19)

Under a nitrogen gas atmosphere, 15.0 g (49.3 mmol) of the compound (19), 150 mL of tetrahydrofuran, and 7.00 mL of allyl glycidyl ether were added to a 500 mL eggplant-shaped flask, and the mixture was stirred until homogeneous. 6.00 g of t-BuOK was added to this homogeneous solution, and the reaction was carried out by being stirred at 70° C. for 4 hours. The obtained reaction product was cooled to 25° C. and tetrahydrofuran was distilled off. Toluene was added to the residue, washed with water, and dehydrated with anhydrous sodium sulfate. After filtering off the drying agent, the filtrate was concentrated and the residue was purified by silica gel column chromatography to obtain 12.0 g of a compound represented by Formula (20).

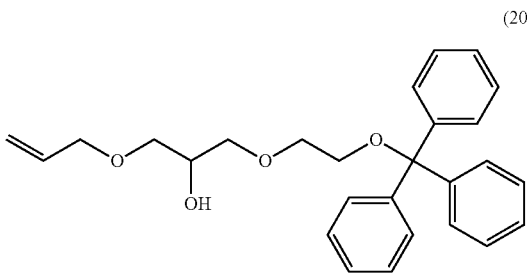

(20)

5.00 g of the compound represented by Formula (20), 50 mL of dichloromethane, and 5.00 g of metachloroperbenzoic acid were added under ice cooling to a 300 mL eggplant-shaped flask, and the mixture was stirred at the same temperature for 1 hour and at room temperature for 12 hours. 10 mL of a saturated sodium sulfite aqueous solution was added to the reaction solution under ice cooling, the mixture was stirred for 30 minutes, and then stirred at room temperature for 30 minutes. The solution was transferred to a separatory funnel, and the organic layer was washed with water and dehydrated with anhydrous sodium sulfate. After filtering off the drying agent, the filtrate was concentrated and the residue was purified by silica gel column chromatography to obtain 4.50 g of compound (21).

$^1$H-NMR measurement of the obtained compound (21) was performed, and the structure was identified based on the following results.

Compound (21) $^1$H-NMR (CDCl$_3$);

δ [ppm] 2.62 (1H), 2.81 (1H), 3.18 (1H), 3.28 (2H), 3.48 (1H), 3.50 to 3.75 (6H), 3.85 (1H), 4.03 (1H), 7.18 to 7.38 (9H), 7.45 (6H)

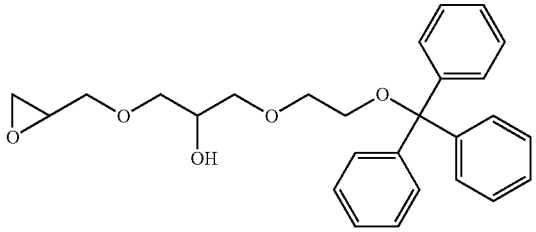

(21)

Under a nitrogen gas atmosphere, 5.98 g of the compound represented by Formula (18) obtained as described above, 1.52 g of the compound represented by Formula (21), and 30 mL of t-BuOH were added to a 100 mL eggplant-shaped flask, and the mixture was stirred at room temperature until homogeneous. 0.200 g (1.78 mmol) of t-BuOK was added to this homogeneous solution and reacted by being stirred at 70° C. for 12 hours. The obtained reaction product was cooled to 25° C. and neutralized with 0.1 mol/L hydrochloric acid. After that, extraction was carried out with Vertrel XF, and the organic layer was washed with water and dehydrated with anhydrous sodium sulfate. After filtering off the drying agent, the filtrate was concentrated.

8 mL of Vertrel XF, 0.75 mL of water, and 7.5 mL of trifluoroacetic acid were added at room temperature to the obtained residue, and the mixture was stirred at room temperature for 1 hour. Vertrel XF, Water, and trifluoroacetic acid were distilled off at 35° C. or lower, 30 mL of 5% aqueous sodium bicarbonate solution was added to the obtained residue, and extraction was carried out with Vertrel XF and the organic layer was washed with water and concentrated. 5 mL of methanol and 14 mL of 1 mol/L sodium hydroxide aqueous solution were added to the obtained residue, and the mixture was stirred at room temperature for 1 hour. Methanol was distilled off and extraction was carried out with Vertrel XF and the organic layer was washed with 1 mol/L hydrochloric acid and water and dehydrated with anhydrous sodium sulfate. After filtering off the drying agent, the filtrate was concentrated and the residue was purified by silica gel column chromatography to obtain 3.30 g of compound (I).

$^1$H-NMR measurement of the obtained compound (I) was performed, and the structure was identified based on the following results.

Compound (I); $^1$H-NMR (C$_6$F$_6$/CD$_3$COCD$_3$=4/1 (V/V));

δ [ppm] δ [ppm] 3.45 to 3.90 (14H), 3.95 to 4.15 (4H), 4.90 (2H), 7.45 to 7.75 (5H)

Example 10

The same operations as in Example 9 were performed except that 4.42 g of a compound represented by Formula (22) was used instead of the compound represented by Formula (17) to obtain 3.40 g of a compound (J).

$^1$H-NMR measurement of the obtained compound (J) was performed, and the structure was identified based on the following results.

Compound (J): $^1$H-NMR (C$_6$F$_6$/CD$_3$COCD$_3$=4/1 (V/V));

δ [ppm] 3.45 to 3.90 (14H), 3.95 to 4.15 (4H), 4.95 (2H), 7.45 to 7.75 (7H)

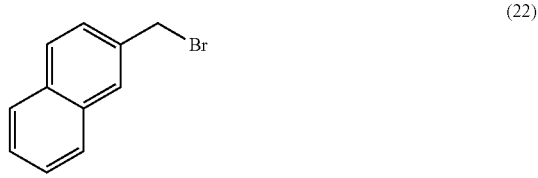 [SMILES: BrCc1ccc2ccccc2c1]

(22)

Example 11

The same operations as in Example 9 were performed except that 2.42 g of a compound represented by Formula (23) was used instead of the compound represented by Formula (17) to obtain 3.02 g of the compound (K).

$^1$H-NMR measurement of the obtained compound (K) was performed, and the structure was identified based on the following results.

Compound (K): $^1$H-NMR (C$_6$F$_6$/CD$_3$COCD$_3$=4/1(V/V));

δ [ppm] 3.45 to 3.90 (14H), 3.95 to 4.15 (6H), 5.10 to 5.30 (2H), 5.90 to 6.00 (1H)

(23)

Example 12

Under a nitrogen gas atmosphere, 4.90 g of the compound represented by Formula (8) obtained as described above, 45 mL of t-BuOH, and 2.30 g of epibromohydrin were added to a 200 mL eggplant-shaped flask and stirred until homogeneous. 0.500 g of t-BuOK was added to this homogeneous solution, and the mixture was reacted by being stirred at 70° C. for 6 hours. The obtained reaction product was cooled to 25° C., neutralized with 0.1 mol/L hydrochloric acid, and then extraction was carried out with Vertrel XF, and the organic layer was washed with water and dehydrated with anhydrous sodium sulfate. After filtering off the drying agent, the filtrate was concentrated and the residue was purified by silica gel column chromatography to obtain 5.00 g of a compound represented by Formula (24).

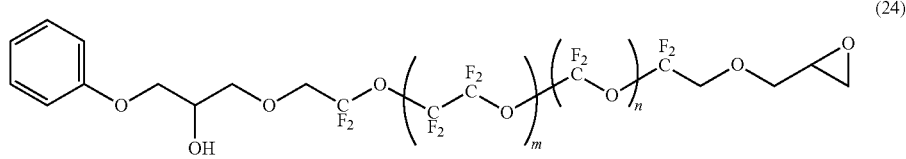

(24)

(In Formula (24), m is 6 and n is 6.)

Under a nitrogen gas atmosphere, 3.19 g of the compound represented by Formula (24), 28 mL of t-BuOH, and 3.50 g of propylene glycol were added to a 100 mL eggplant-shaped flask, and the mixture was stirred until homogeneous. 0.700 g of t-BuOK was added to this homogeneous solution, and the mixture was reacted by being stirred at 70° C. for 6 hours. The obtained reaction product was cooled to 25° C., neutralized with 0.1 mol/L hydrochloric acid, extraction was carried out with Vertrel XF, and the organic layer was washed with water and dehydrated with anhydrous sodium sulfate. After filtering off the drying agent, the filtrate was concentrated and the residue was purified by silica gel column chromatography to obtain 2.14 g of compound (L).

$^1$H-NMR measurement of the obtained compound (L) was performed, and the structure was identified based on the following results.

Compound (L): $^1$H-NMR ($C_6F_6/CD_3COCD_3=4/1$ (V/V)): δ [ppm] 1.79 (2H), 3.40 to 3.55 (3H), 3.55 to 3.90 (11H), 3.95 to 4.15 (4H), 6.80 to 7.30 (5H)

Example 13

The same operations as in Example 12 were performed except that 5.00 g of a compound represented by Formula (25) as a synthetic intermediate of Example 2 was used instead of the compound represented by Formula (8) to obtain 2.34 g of compound (M).

$^1$H-NMR measurement of the obtained compound (M) was performed, and the structure was identified based on the following results.

Compound (M): $^1$H-NMR ($C_6F/CD_3COCD_3=4/1$ (V/V)); δ [ppm] 1.79 (2H), 3.45 to 3.60 (3H), 3.60 to 4.00 (14H), 3.95 to 4.15 (4H), 6.75 to 6.85 (2H), 7.10 to 7.20 (2H)

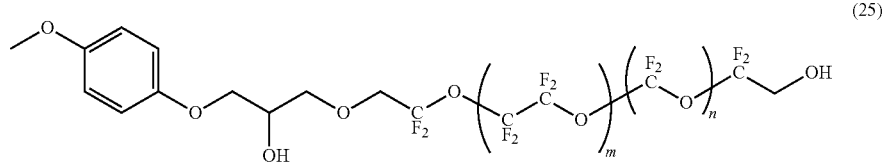

(25)

(In Formula (25), m is 6 and n is 6.)

Example 14

The same operations as in Example 12 were performed except that 5.02 g of a compound represented by Formula (26) as a synthetic intermediate of Example 4 was used instead of the compound represented by Formula (8) to obtain 2.26 g of compound (N).

$^1$H-NMR measurement of the obtained compound (N) was performed, and the structure was identified based on the following results.

Compound (N): $^1$H-NMR ($C_6F_6$/$CD_3COCD_3$=4/1(V/V));
δ [ppm]=1.79 (2H), 3.15 (2H), 3.40 to 3.55 (8H), 3.60 to 3.95 (8H), 4.00 to 4.15 (4H), 6.80 (2H), 7.05 (1H)

1,4-diol were added to a 100 mL eggplant-shaped flask and stirred until homogeneous. 0.112 g of t-BuOK was added to this homogeneous solution, and the mixture was reacted by being stirred at 70° C. for 6 hours. The obtained reaction product was cooled to 25° C., neutralized with 0.1 mol/L hydrochloric acid, extraction was carried out with Vertrel XF, and the organic layer was washed with water and dehydrated with anhydrous sodium sulfate. After filtering off the drying agent, the filtrate was concentrated and the residue was purified by silica gel column chromatography to obtain 2.32 g of compound (P).

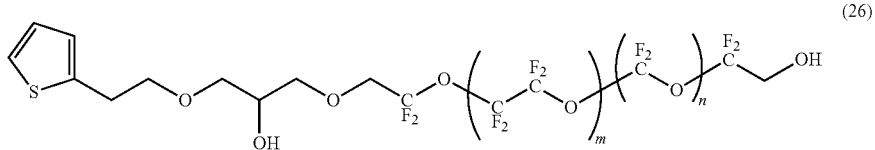

(26)

(In Formula (26), m is 6 and n is 6.)

Example 15

The same operations as in Example 12 were performed except that 4.77 g of a compound represented by Formula (27) as a synthetic intermediate of Example 8 was used instead of the compound represented by Formula (8) to obtain 2.33 g of compound (O).

$^1$H-NMR measurement of the obtained compound (O) was performed, and the structure was identified based on the following results.

Compound (O); $^1$H-NMR ($C_6F_6$/$CD_3COCD_3$=4/1(V/V));
δ [ppm] 1.79 (2H), 3.45 to 3.90 (14H), 3.95 to 4.15 (6H), 5.10 to 5.30 (2H), 5.90 to 6.00 (1H)

$^1$H-NMR measurement of the obtained compound (P) was performed, and the structure was identified based on the following results.

Compound (P): $^1$H-NMR ($C_6F_6$/$CD_3COCD_3$=4/1 (V/V));
δ [ppm] 3.40 to 3.55 (3H), 3.55 to 3.95 (11H), 4.00 to 4.20 (4H), 6.80 to 7.30 (5H)

Example 17

The same operations as in Example 16 were performed except that 3.26 g of a compound represented by Formula (28) as a synthetic intermediate of Example 13 was used instead of the compound represented by Formula (24) to obtain 2.38 g of the compound (Q).

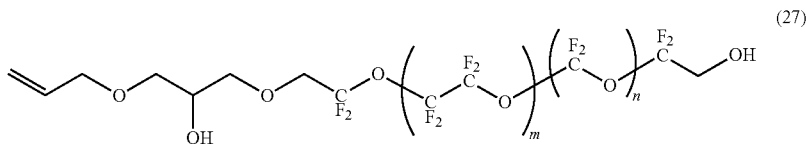

(27)

(In Formula (27), m is 6 and n is 6.)

Example 16

Under a nitrogen gas atmosphere, 3.19 g of the compound represented by Formula (24) obtained as described above, 28 mL of t-BuOH, and 4.00 g of 2,2,3,3-tetrafluorobutane- $^1$H-NMR measurement of the obtained compound (Q) was performed and the structure was identified based on the following results.

Compound (Q); $^1$H-NMR ($C_6F_6$/$CD_3COCD_3$=4/1(V/V)):
δ [ppm] 3.45 to 3.60 (3H), 3.60 to 4.00 (14H), 4.00 to 4.20 (4H), 6.75 to 6.85 (2H), 7.10 to 7.20 (2H)

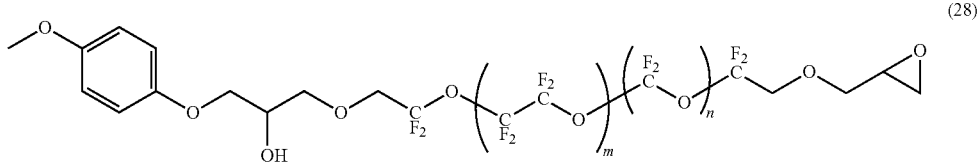

(In Formula (28), m is 6 and n is 6.)

Example 18

The same operations as in Example 16 were performed except that 3.26 g of a compound represented by Formula (29) as a synthetic intermediate of Example 14 was used instead of the compound represented by Formula (24) to obtain 2.21 g of the compound (R).

$^1$H-NMR measurement of the obtained compound (R) was performed, and the structure was identified based on the following results.

Compound (R): $^1$H-NMR ($C_6F_6/CD_3COCD_3$=4/1(V/V));
δ [ppm]=3.15 (2H), 3.40 to 3.55 (8H), 3.60 to 3.95 (8H), 4.00 to 4.15 (4H), 6.80 (2H), 7.05 (1H)

this solution under ice cooling, the mixture was stirred at the same temperature for 1 hour, and further stirred at room temperature for 10 hours. Thereafter, 20 mL of a saturated sodium hydrogen carbonate aqueous solution and 20 mL of a saturated sodium sulfite aqueous solution were added thereto under ice cooling, and the mixture was stirred at the same temperature for 30 minutes. The aqueous layer was separated from the reaction solution, and the organic layer was washed with water and dehydrated with anhydrous sodium sulfate. After filtering off the drying agent, the filtrate was concentrated, and the residue was purified by silica gel column chromatography to obtain 6.40 g of compound (31).

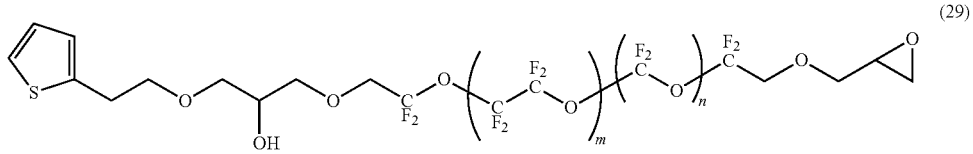

(In Formula (29), m is 6 and n is 6.)

Example 19

The same operations as in Example 16 were performed except that 3.12 g of a compound represented by Formula (30) as a synthetic intermediate of Example 15 was used instead of the compound represented by Formula (24) to obtain 2.28 g of compound (S).

$^1$H-NMR measurement of the obtained compound (S) was performed, and the structure was identified based on the following results.

Compound (S): $^1$H-NMR ($C_6F_6/CD_3COCD_3$=4/1 (V/V)):
δ [ppm]=3.40 to 3.55 (3H), 3.60 to 3.95 (11H), 4.00 to 4.15 (6H), 5.15 (2H), 5.30 (1H), 5.90 to 6.00 (1H)

$^1$H-NMR measurement of the obtained compound (31) was performed, and the structure was identified based on the following results.

Compound (31) $^1$H-NMR ($C_6F_6/CD_3COCD_3$=4/1(V/V));
δ [ppm] 1.73 (1H), 1.88 (1H), 2.01 (3H), 2.41 (1H), 2.67 (1H), 2.88 (1H), 4.12 (2H)

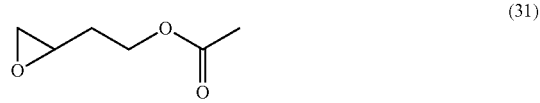

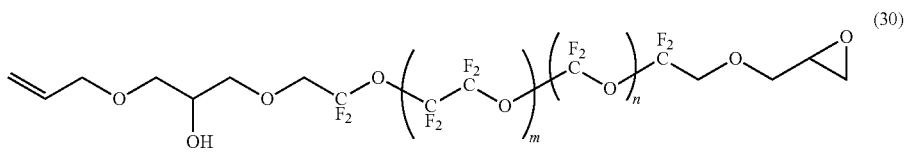

(In Formula (30), m is 6 and n is 6.)

Example 20

3-butenyl acetate (12.0 g) and 100 mL of dichloromethane were added to a 500 mL eggplant-shaped flask, and the mixture was stirred at room temperature to obtain a uniform solution. 31.0 g of m-chloroperbenzoic acid was added to Under a nitrogen gas atmosphere, 7.10 g of the compound represented by Formula (8), 0.781 g of the compound represented by Formula (31), and 50 mL of t-BuOH were added to a 200 mL eggplant-shaped flask and stirred until homogeneous at room temperature. 0.225 g of t-BuOK was added to this homogeneous solution, and the mixture was reacted by being stirred at 70° C. for 30 hours. The obtained reaction product was cooled to 25° C., neutralized with 0.1 mol/L hydrochloric acid, extraction was carried out with Vertrel XF, and the organic layer was washed with water and dehydrated with anhydrous sodium sulfate. After filtering off the drying agent, the filtrate was concentrated.

30 mL of methanol and 30 mL of a 1 mol/L sodium hydroxide aqueous solution were added to the obtained residue at room temperature, and the mixture was stirred at room temperature for 1 hour. The methanol was distilled off, extraction was carried out with Vertrel XF, and the organic layer was washed with water and dehydrated with anhydrous sodium sulfate. After filtering off the drying agent, the filtrate was concentrated and the residue was purified by silica gel column chromatography to obtain 4.62 g of compound (T).

$^1$H-NMR measurement of the obtained compound (T) was performed, and the structure was identified based on the following results.

Compound (T); $_1$H-NMR (C$_6$F$_6$/CD$_3$COCD$_3$=4/1 (V/V)):

δ [ppm] 1.54 to 1.76 (2H), 3.55 to 3.80 (5H), 3.82 to 4.20 (9H), 6.80 to 7.30 (5H)

Example 21

The same operations as in Example 20 were performed except that 7.25 g of a compound represented by Formula (25) was used instead of the compound represented by Formula (8) to obtain 5.02 g of the compound (U).

$^1$H-NMR measurement of the obtained compound (U) was performed, and the structure was identified based on the following results.

Compound (U): $^1$H-NMR (C$_6$F$_6$/CD$_3$COCD$_3$=4/1 (V/V));

δ [ppm] 1.54 to 1.76 (2H), 3.55 to 3.80 (8H), 3.82 to 4.20 (9H), 6.55 to 6.60 (2H), 6.70 to 6.75 (2H)

Example 22

The same operations as in Example 20 were performed except that 7.35 g of a compound represented by Formula (32) as the intermediate of Example 10 was used instead of the compound represented by Formula (8) to obtain 4.89 g of the compound (V).

$^1$H-NMR measurement of the obtained compound (V) was performed, and the structure was identified based on the following results.

Compound (V): $^1$H-NMR (C$_6$F$_6$/CD$_3$COCD$_3$=4/1(V/V));

δ [ppm] 1.54 to 1.76 (2H), 3.55 to 3.80 (5H), 3.82 to 4.20 (9H), 7.00 to 7.50 (7H)

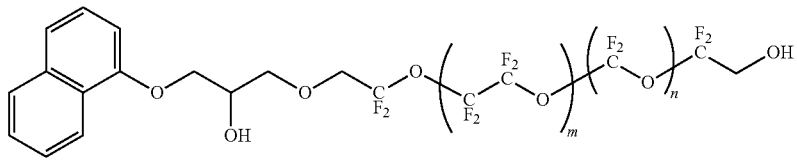

(32)

(In Formula (32), m is 6 and n is 6.)

Example 23

The same operations as in Example 20 were performed except that 7.27 g of a compound represented by Formula (26) was used instead of the compound represented by Formula (8) to obtain 4.55 g of the compound (W).

$^1$H-NMR measurement of the obtained compound (W) was performed, and the structure was identified based on the following results.

Compound (W), $^1$H-NMR (C$_6$F$_6$/CD$_3$COCD$_3$=4/1 (V/V));

δ [ppm] 1.54 to 1.76 (2H), 3.55 to 3.80 (5H), 3.80 to 4.20 (9H), 6.80 (2H), 7.05 (1H)

Example 24

The same operations as in Example 20 were performed except that 7.35 g of a compound represented by Formula (33) as the intermediate of Example 6 was used instead of the compound represented by Formula (8) to obtain 4.24 g of the compound (X).

$^1$H-NMR measurement of the obtained compound (X) was performed, and the structure was identified based on the following results.

Compound (X); $^1$H-NMR (C$_6$F$_6$/CD$_3$COCD$_3$=4/1(V/V));

δ [ppm] 1.54 to 1.76 (2H), 2.35 (3H), 3.00 (2H), 3.55 to 3.80 (5H), 3.82 to 4.20 (1H), 8.40 (1H)

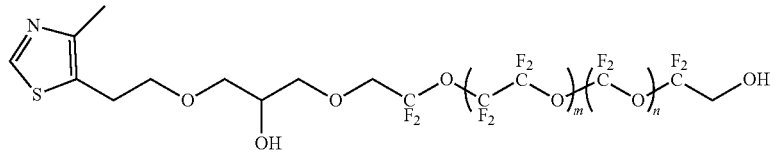

(33)

(In Formula (33), m is 6 and n is 6.)

Example 25

The same operations as in Example 20 were performed except that 6.92 g of a compound represented by Formula (27) was used instead of the compound represented by Formula (8) to obtain 4.66 g of the compound (Y).

$^1$H-NMR measurement of the obtained compound (Y) was performed, and the structure was identified based on the following results.

Compound (Y); ¹H-NMR (C₆F₆/CD₃COCD₃=4/1(V/V));
δ [ppm] 1.54 to 1.76 (2H), 3.55 to 3.80 (5H), 3.82 to 4.20 (11H), 5.20 to 5.30 (2H), 5.80 to 5.90 (1H)

Example 26

Under a nitrogen gas atmosphere, 22.1 g of a compound (number average molecular weight 1106, molecular weight distribution 1.1) represented by HOCH₂CF₂O(CF₂CF₂O)ₓCF₂CH₂OH (in the formula, x is 8), 1.50 g of compound (7), and 10 mL of t-BuOH were added to a 200 mL eggplant-shaped flask, and the mixture was stirred at room temperature until homogeneous. 0.900 g of t-BuOK was added to this homogeneous solution, and the mixture was reacted by being stirred at 70° C. for 8 hours. The obtained reaction product was cooled to 25° C., neutralized with 0.5 mol/L hydrochloric acid, extraction was carried out with Vertrel XF, and the organic layer was washed with water and dehydrated with anhydrous sodium sulfate. After filtering off the drying agent, the filtrate was concentrated, and the residue was purified by silica gel column chromatography to obtain 6.29 g of compound (34).

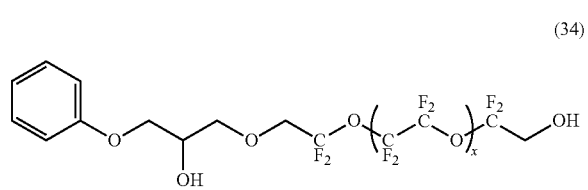

(34)

(In Formula (34), x is 8.)

Under a nitrogen gas atmosphere, 6.28 g of the compound represented by Formula (34) obtained as described above, 1.05 g of the compound represented by Formula (9), and 50 mL of t-BuOH were added to a 200 mL eggplant-shaped flask, and the mixture was stirred at room temperature until homogeneous. 0.224 g of t-BuOK was added to this homogeneous solution, and the mixture was reacted by being stirred at 70° C. for 16 hours. The obtained reaction product was cooled to 25° C., neutralized with 0.1 mol/L hydrochloric acid, extraction was carried out with Vertrel XF, and the organic layer was washed with water and dehydrated with anhydrous sodium sulfate. After filtering off the drying agent, the filtrate was concentrated.

0.75 mL of water and 7.5 mL of trifluoroacetic acid were added to the obtained residue at room temperature, and the mixture was stirred at room temperature for 6 hours. Water and trifluoroacetic acid were distilled off at 35° C. or lower, 30 mL of a 5% aqueous sodium bicarbonate solution was added to the obtained residue, extraction was carried out with Vertrel XF, and the organic layer was washed with water and concentrated. 5 mL of methanol and 20 mL of 1 mol/L sodium hydroxide aqueous solution were added to the obtained residue, and the mixture was stirred at room temperature for 1 hour. The methanol was distilled off, extraction was carried out with Vertrel XF, and the organic layer was washed with water and dehydrated with anhydrous sodium sulfate. After filtering off the drying agent, the filtrate was concentrated, and the residue was purified by silica gel column chromatography to obtain 4.28 g of compound (Z).

¹H-NMR measurement of the obtained compound (Z) was performed, and the structure was identified based on the following results.

Compound (Z); ¹H-NMR (C₆F₆/CD₃COCD₃=4/1 (V/V)):
δ [ppm] 3.40 to 3.55 (3H), 3.88 to 4.20 (15H), 6.90 to 7.20 (5H)

Example 27

The same operations as in Example 1 were performed except that 1.12 g of a compound represented by Formula (35) was used instead of the compound represented by Formula (7) to obtain 4.05 g of the compound (AB).

¹H-NMR measurement of the obtained compound (AB) was performed, and the structure was identified based on the following results.

Compound (AB); ¹H-NMR (CD₃COCD₃);
δ [ppm] 2.50 (1H), 3.45 to 3.65 (8H), 3.65 to 3.90 (6H), 4.00 to 4.20 (6H)

(35)

Example 28

The same operations as in Example 1 were performed except that 1.88 g of a compound represented by Formula (36) was used instead of the compound represented by Formula (7) to obtain 3.85 g of the compound (AC). Here, the compound represented by Formula (36) was synthesized by oxidizing only one side of glycerin diallyl ether.

¹H-NMR measurement of the obtained compound (AC) was performed, and the structure was identified based on the following results.

Compound (AC); ¹H-NMR (CD₃COCD₃):
δ [ppm] 3.35 to 3.95 (19H), 3.95 to 4.15 (6H), 5.05 to 5.15 (1H), 5.20 to 5.30 (1H), 5.80 to 6.00 (1H)

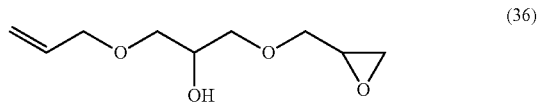

(36)

Comparative Example 1

A compound represented by Formula (AA) was synthesized by the method described in Patent Document 1.

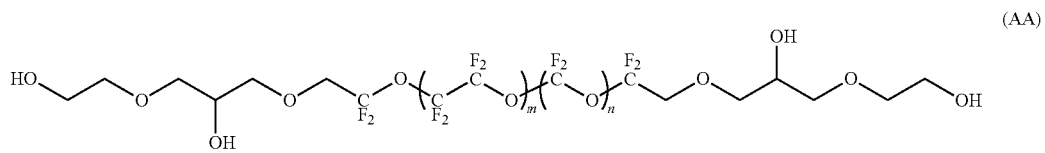

(AA)

(In Formula (AA), m is 6 and n is 6.)

Comparative Example 2

A compound represented by Formula (BB) was synthesized by the method described in Patent Document 2.

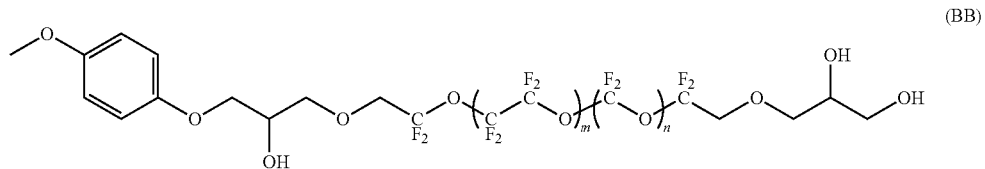
(BB)

(In Formula (BB), m is 6 and n is 6.)

Comparative Example 3

A compound represented by Formula (CC) was synthesized by the method described in Patent Document 3.

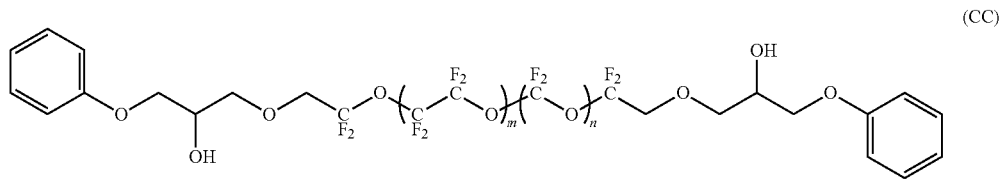
(CC)

(In Formula (CC), m is 6 and n is 6.)

The structures of $R^1$ to $R^4$ when applying the compounds of Examples 1 to 28 and Comparative Examples 1 to 3 obtained in this manner to Formula (1) are shown in Tables 1 to 4. In addition, the number average molecular weights of the compounds of Examples 1 to 26 and Comparative Examples 1 to 3 were determined by the $^1$H-NMR and $^{19}$F-NMR measurement described above. The results are shown in Tables 1 to 4.

TABLE 1

| Example | Compound | R1 | R2 | R3 | R4 | Molecular weight |
|---|---|---|---|---|---|---|
| 1 | A | phenyl- | Formula (6) w = 1 | Formula (3) m = 6, n = 6 | Formula (2-1) p1 = 1, P2 = 1 | 1538 |
| 2 | B | H₃CO-phenyl- | Formula (6) w = 1 | Formula (3) m = 6, n = 6 | Formula (2-1) p1 = 1, P2 = 1 | 1568 |
| 3 | C | naphthyl- | Formula (6) w = 1 | Formula (3) m = 6, n = 6 | Formula (2-1) p1 = 1, P2 = 1 | 1588 |
| 4 | D | thienyl-CH₂- | Formula (6) w = 1 | Formula (3) m = 6, n = 6 | Formula (2-1) p1 = 1, P2 = 1 | 1572 |

TABLE 1-continued

| Example | Compound | R1 | R2 | R3 | R4 | Molecular weight |
|---|---|---|---|---|---|---|
| 5 | E | (1-methyl-pyrazol-5-yl)-CH2– | Formula (6) w = 1 | Formula (3) m = 6, n = 6 | Formula (2-1) p1 = 1, P2 = 1 | 1556 |
| 6 | F | (4-methyl-thiazol-5-yl)-CH2CH2– | Formula (6) w = 1 | Formula (3) m = 6, n = 6 | Formula (2-1) p1 = 1, P2 = 1 | 1587 |
| 7 | G | (furan-3-yl)-CH2– | Formula (6) w = 1 | Formula (3) m = 6, n = 6 | Formula (2-1) p1 = 1, P2 = 1 | 1542 |

TABLE 2

| Example | Compound | R1 | R2 | R3 | R4 | Molecular weight |
|---|---|---|---|---|---|---|
| 8 | H | allyl– | Formula (6) w = 1 | Formula (3) m = 6, n = 8 | Formula (2-1) p1 = 1, P2 = 1 | 1502 |
| 9 | I | benzyl– | 0 | Formula (3) m = 4, 5, n = 4, 5 | Formula (2-1) p1 = 1, P2 = 1 | 1279 |
| 10 | J | (naphthalen-2-yl)-CH2– | 0 | Formula (3) m = 4, 5, n = 4, 5 | Formula (2-1) p1 = 2, P2 = 1 | 1329 |
| 11 | K | allyl– | 0 | Formula (3) m = 4, 5, n = 4, 5 | Formula (2-1) p1 = 2, P2 = 1 | 1229 |
| 12 | L | phenyl– | Formula (6) w = 1 | Formula (3) m = 6, n = 6 | Formula (2-4) q = 2 | 1552 |
| 13 | M | 4-methoxyphenyl– | Formula (6) w = 1 | Formula (3) m = 6, n = 6 | Formula (2-4) q = 2 | 1582 |
| 14 | N | (thiophen-2-yl)-CH2CH2– | Formula (6) w = 1 | Formula (3) m = 6, n = 6 | Formula (3-4) q = 2 | 1586 |

TABLE 3

| Example | Compound | R1 | R2 | R3 | R4 | Molecular weight |
|---|---|---|---|---|---|---|
| 15 | O | allyl– | Formula (6) w = 1 | Formula (3) m = 6, n = 6 | Formula (2-4) q = 2 | 1516 |
| 16 | P | phenyl– | Formula (6) w = 1 | Formula (3) m = 6, n = 6 | Formula (2-2) S = 2 | 1638 |

TABLE 3-continued

| Example | Compound | R1 | R2 | R3 | R4 | Molecular weight |
|---|---|---|---|---|---|---|
| 17 | Q | H$_3$CO—C$_6$H$_4$— | Formula (6) w = 1 | Formula (3) m = 6, n = 6 | Formula (2-2) S = 2 | 1668 |
| 18 | R | 2-thienyl-CH$_2$— | Formula (6) w = 1 | Formula (3) m = 6, n = 6 | Formula (2-2) S = 2 | 1672 |
| 19 | S | allyl— | Formula (6) w = 1 | Formula (3) m = 6, n = 6 | Formula (2-2) S = 2 | 1602 |
| 20 | T | phenyl— | Formula (6) w = 1 | Formula (3) m = 6, n = 6 | Formula (2-3) t = 1 | 1508 |
| 21 | U | H$_3$CO—C$_6$H$_4$— | Formula (6) w = 1 | Formula (3) m = 6, n = 6 | Formula (2-3) t = 1 | 1538 |

TABLE 4

| Example | Compound | R1 | R2 | R3 | R4 | Molecular weight |
|---|---|---|---|---|---|---|
| 22 | V | naphthyl— | Formula (6) w = 1 | Formula (3) m = 6, n = 6 | Formula (2-3) t = 1 | 1558 |
| 23 | W | 2-thienyl-CH$_2$— | Formula (6) w = 1 | Formula (3) m = 6, n = 6 | Formula (2-3) t = 1 | 1542 |
| 24 | X | 4-methylthiazol-5-yl-CH$_2$— | Formula (6) w = 1 | Formula (3) m = 6, n = 6 | Formula (2-3) t = 1 | 1557 |
| 25 | Y | allyl— | Formula (6) w = 1 | Formula (3) m = 6, n = 6 | Formula (2-3) t = 1 | 1472 |
| 26 | Z | phenyl— | Formula (6) w = 1 | Formula (3) m = 8, n = 0 | Formula (2-1) p1 = 1, P2 = 1 | 1374 |
| 27 | AB | propargyl— | Formula (6) w = 1 | Formula (3) m = 6, n = 6 | Formula (2-1) p1 = 1, P2 = 1 | 1500 |
| 28 | AC | allyl— | Formula (6) w = 2 | Formula (3) m = 6, n = 6 | Formula (2-1) p1 = 1, P2 = 1 | 1576 |

Next, a solution for forming a lubricating layer was prepared by using the compounds obtained in Examples 1 to 28 and Comparative Examples 1 to 3 by the following method. Using the obtained solution for forming a lubricating layer, a lubricating layer of a magnetic recording medium was formed by the following method and the magnetic recording media of Examples 1 to 28 and Comparative Examples 1 to 3 were obtained.

[Solution for Forming Lubricating Layer]

The compounds obtained in Examples 1 to 28 and Comparative Examples 1 to 3 were each dissolved in Vertrel (registered trademark) XF (trade name, manufactured by Du Pont-Mitsui Fluorochemicals Co., Ltd.) which is a fluorine-based solvent, and diluted with Vertrel such that the thickness when coated on the protective layer was 9 Å to 11 Å, and a solution for forming a lubricating layer was obtained in which the concentration of the compound was 0.0005 mass % to 0.001 mass %.

[Magnetic Recording Medium]

A magnetic recording medium was prepared in which an adhesive layer, a soft magnetic layer, a first underlayer, a second underlayer, a magnetic layer, and a protective layer were provided in order on a substrate having a diameter of 65 mm. The protective layer was formed of carbon.

The solutions for forming a lubricating layer of Examples 1 to 28 and Comparative Examples 1 to 3 were respectively coated by a dipping method onto the protective layer of the magnetic recording medium on which the respective layers up to the protective layer were formed. Here, the dipping method was carried out under conditions of an immersion speed of 10 mm/sec, an immersion time of 30 sec, and a pulling rate of 1.2 mm/sec.

Thereafter, the magnetic recording medium coated with the solution for forming a lubricating layer was placed in a constant temperature oven at 120° C. and heated for 10 minutes to remove the solvent in the solution for forming a lubricating layer to form a lubricating layer on the protective layer and obtain a magnetic recording medium.

The thicknesses of the lubricating layers of the magnetic recording media of Examples 1 to 28 and Comparative Examples 1 to 3 obtained in this manner were measured using FT-IR (trade name: Nicolet iS 50, manufactured by Thermo Fisher Scientific). The results are shown in Table 5.

Next, the chemical resistance tests shown below were carried out on the magnetic recording media of Examples 1 to 28 and Comparative Examples 1 to 3.

(Chemical Resistance Test)

This evaluation method is for investigating contamination of magnetic recording media by environmental substances which generate contaminants in high temperature environments. In the environmental resistance evaluation method shown below, using Si ions as an environmental substance, the Si adsorption amount was measured as the amount of contaminant contaminating the magnetic recording medium generated by the environmental substance.

Specifically, the magnetic recording medium to be evaluated was held for 240 hours in the presence of a siloxane-based Si rubber in a high-temperature environment at a temperature of 85° C. and a humidity of 0%. Next, the Si adsorption amount present on the surface of the magnetic recording medium was analytically measured by secondary ion mass spectrometry (SIMS), and the extent of contamination by Si ions was evaluated as the Si adsorption amount. The Si adsorption amount was evaluated by using a numerical value with the result of Comparative Example 2 set to 1.00. The results are shown in Table 5.

TABLE 5

| | Compound | Thickness (Å) | Chemical resistance evaluation | Friction coefficient increase time (sec) |
|---|---|---|---|---|
| Example 1 | A | 9.5 | 0.65 | A |
| Example 2 | B | 9.5 | 0.61 | A |
| Example 3 | C | 9.5 | 0.69 | A |
| Example 4 | D | 9.0 | 0.60 | A |
| Example 5 | E | 9.0 | 0.61 | A |
| Example 6 | F | 9.0 | 0.64 | A |
| Example 7 | G | 9.5 | 0.68 | A |
| Example 8 | H | 9.0 | 0.59 | B |
| Example 9 | I | 9.5 | 0.71 | B |
| Example 10 | J | 9.5 | 0.73 | A |
| Example 11 | K | 9.0 | 0.69 | B |
| Example 12 | L | 9.5 | 0.65 | A |
| Example 13 | M | 9.5 | 0.63 | A |
| Example 14 | N | 9.0 | 0.60 | A |
| Example 15 | O | 9.0 | 0.59 | B |
| Example 16 | P | 9.5 | 0.64 | B |
| Example 17 | Q | 9.5 | 0.62 | B |
| Example 18 | R | 9.0 | 0.59 | B |
| Example 19 | S | 9.0 | 0.61 | B |
| Example 20 | T | 9.5 | 0.67 | A |
| Example 21 | U | 9.5 | 0.63 | A |
| Example 22 | V | 9.5 | 0.70 | A |
| Example 23 | W | 9.0 | 0.59 | A |
| Example 24 | X | 9.5 | 0.61 | A |
| Example 25 | Y | 9.0 | 0.61 | B |
| Example 26 | Z | 9.0 | 0.63 | B |
| Example 27 | AB | 9.0 | 0.60 | B |
| Example 28 | AC | 9.5 | 0.56 | B |
| Comparative Example 1 | AA | 10.5 | 0.80 | X |
| Comparative Example 2 | BB | 10.5 | 1.00 | C |
| Comparative Example 3 | CC | 10.5 | 1.02 | C |

It is apparent from Table 5 that in comparison with the magnetic recording media of Comparative Examples 1 to 3, in the magnetic recording media of Examples 1 to 28, regardless of whether the lubricating layer is thin, the Si adsorption amount is small and the magnetic recording media of Examples 1 to 28 are not easily contaminated by environmental substances in a high temperature environment.

In addition, in Example 2, the carbon atoms to which a hydroxyl group is bonded in $R^4$ in the compound represented by Formula (1) forming the lubricating layer may be bonded to each other via a linking group including a carbon atom not bonded with a hydroxyl group. On the other hand, in Comparative Example 2, the carbon atoms to which hydroxyl groups are bonded in $R^4$ in the compound represented by Formula (1) forming the lubricating layer may be bonded to each other. From the results of Example 2 and Comparative Example 2 shown in Table 5, it is understood that, since the carbon atoms to which hydroxyl groups are bonded in $R^1$ are bonded to each other via a linking group including a carbon atom not bonded with a hydroxyl group, the chemical resistance is improved.

In addition, the wear resistance tests shown below were carried out on the magnetic recording media of Examples 1 to 28 and Comparative Examples 1 to 3.

(Wear Resistance Test)

Using a pin-on-disk friction wear resistance tester, a ball of alumina having a diameter of 2 mm as a contact was slid on the lubricating layer of the magnetic recording medium at a load of 40 gf and a sliding speed of 0.25 m/sec and the friction coefficient of the surface of the lubricating layer was measured. Then, the sliding time until the friction coefficient of the surface of the lubricating layer abruptly increased was measured. The sliding time until the friction coefficient abruptly increased was measured four times for the lubricating layer of each magnetic recording medium and the average value (time) thereof was used as an index of the wear resistance of the lubricant coating layer. The results of the magnetic recording media using the compounds of Examples 1 to 28 and the compounds of Comparative Examples 1 to 3 are shown in Table 5. The evaluation of the friction coefficient increase time was as follows.

A: 650 sec or more

B: 550 sec or more, less than 650 sec
C: 450 sec or more, less than 550 sec
X: Less than 450 sec Here, it is possible to use the time until the friction coefficient abruptly increases as an index of the wear resistance of the lubricating layer for the reasons described below. When wear of the lubricating layer of the magnetic recording medium progresses due to use of the magnetic recording medium and the lubricating layer disappears due to the wear, the contact and the protective layer come into direct contact with each other such that the friction coefficient abruptly increases. In the time until the present friction coefficient abruptly increases, it is considered that there is also a phase which is the friction test.

As shown in Table 5, in the magnetic recording media of Examples 1 to 28, in comparison with the magnetic recording media of Comparative Examples 1 to 3, regardless of whether the lubricating layer was thin, the sliding time until the friction coefficient abruptly increased was long, and the wear resistance was good.

It is presumed that this is because in the magnetic recording media of Examples 1 to 28. $R^1$ in the compound represented by Formula (1) forming the lubricating layer is an end group which includes an organic group having at least one double bond or triple bond.

INDUSTRIAL APPLICABILITY

Using the lubricant for a magnetic recording medium including the fluorine-containing ether compound of the present invention makes it possible to form a lubricating layer capable of realizing excellent chemical resistance and wear resistance even when the thickness is thin.

EXPLANATION OF REFERENCES

10 MAGNETIC RECORDING MEDIUM
11 SUBSTRATE
12 ADHESIVE LAYER
13 SOFT MAGNETIC LAYER
14 FIRST UNDERLAYER
15 SECOND UNDERLAYER
16 MAGNETIC LAYER
17 PROTECTIVE LAYER
18 LUBRICATING LAYER

What is claimed is:

1. A fluorine-containing ether compound represented by Formula (1), $$R^1-R^2-CH_2-R^3-CH_2-R^4 \quad (1)$$

(in Formula (1), $R^1$ is an end group including an organic group having at least one double bond or triple bond and is any one of an end group including an aromatic ring, an end group including a heterocyclic ring, an end group including an alkenyl group, and an end group including an alkynyl group, $R^2$ is a divalent linking group bonded to $R^1$ by etheric oxygen, $R^3$ is a perfluoropolyether chain, $R^4$ is an end group of any one of Formula (2-1) to (2-4)

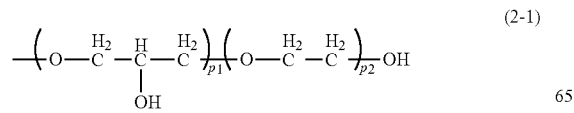
(2-1)

(in Formula (2-1), p1 represents 1 to 2, and p2 represents 1 to 5)

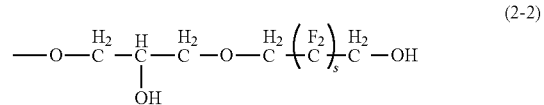
(2-2)

(in Formula (2-2), s represents 2 to 5)

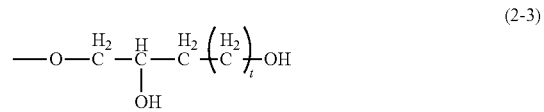
(2-3)

(in Formula (2-3), t represents 1 to 5)

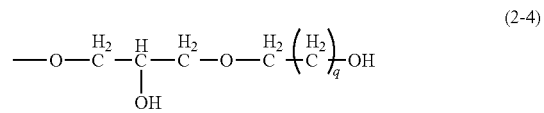
(2-4)

(in Formula (2-4), q represents 2 to 5).

2. The fluorine-containing ether compound according to claim 1,
wherein $R^3$ in Formula (1) is represented by Formula (3)11.11

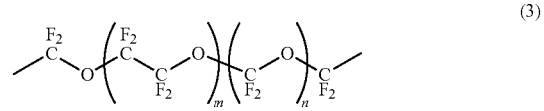
(3)

(in Formula (3), in represents 1 to 30, and n represents 0 to 30).

3. The fluorine-containing ether compound according to claim 1,
wherein $R^3$ in Formula (1) is represented by Formula (4) or Formula (5)

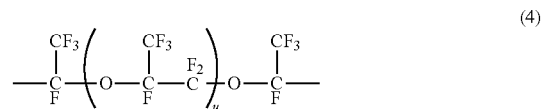
(4)

(in Formula (4), u represents 1 to 30)

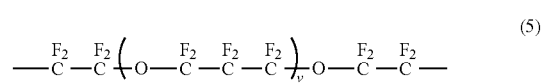
(5)

(in Formula (5), v represents 1 to 30).

4. The fluorine-containing ether compound according to claim 1,
wherein=$R^2$ in Formula (1) is represented by —O— or Formula (6)

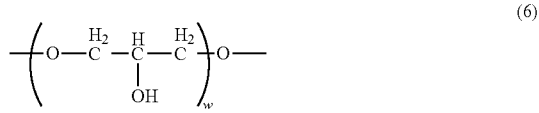

(in Formula (6), w represents 1 to 4).

5. The fluorine-containing ether compound according to claim
wherein $R^4$ in Formula (1) includes three hydroxyl groups.

6. The fluorine-containing ether compound according to claim 1, having a number average molecular weight in a range of 500 to 10,000.

7. A lubricant for a magnetic recording medium comprising:
the fluorine-containing ether compound according to claim 1.

8. A magnetic recording medium comprising:
at least a magnetic layer;
a protective layer; and
a lubricating layer, which are sequentially provided on a substrate,
wherein the lubricating layer includes the fluorine-containing ether compound according to claim 1.

9. The magnetic recording medium according to claim 8,
wherein an average thickness of the lubricating layer is 0.5 nm to 3 nm.

10. The fluorine-containing ether compound according to claim 1, wherein $R^2$ in Formula (1) is —O— or a divalent linking group having 1 to 20 carbon atoms.

* * * * *